US011267738B2

(12) United States Patent
Ghylin

(10) Patent No.: US 11,267,738 B2
(45) Date of Patent: Mar. 8, 2022

(54) METHOD OF USING MICROBIAL DNA SEQUENCING IN RECOVERING RENEWABLE RESOURCES FROM WASTEWATER AND OTHER WASTE STREAMS

(71) Applicant: MICROBE DETECTIVES LLC, Milwaukee, WI (US)

(72) Inventor: Trevor Wayne Ghylin, Wauwatosa, WI (US)

(73) Assignee: MICROBE DETECTIVES LLC, Milwaukee, WI (US)

( * ) Notice: Subject to any disclaimer, the term of this patent is extended or adjusted under 35 U.S.C. 154(b) by 521 days.

(21) Appl. No.: 15/973,269

(22) Filed: May 7, 2018

(65) Prior Publication Data

US 2018/0354830 A1 Dec. 13, 2018

Related U.S. Application Data

(63) Continuation-in-part of application No. 15/961,776, filed on Apr. 24, 2018, now abandoned, which is a continuation-in-part of application No. 15/961,816, filed on Apr. 24, 2018, now abandoned.

(60) Provisional application No. 62/501,857, filed on May 5, 2017, provisional application No. 62/488,918, filed on Apr. 24, 2017, provisional application No. 62/488,913, filed on Apr. 24, 2017.

(51) Int. Cl.
| | |
|---|---|
| *C02F 3/28* | (2006.01) |
| *C02F 3/34* | (2006.01) |
| *C12M 1/107* | (2006.01) |
| *C12Q 1/6888* | (2018.01) |
| *C02F 3/30* | (2006.01) |
| *C12N 1/20* | (2006.01) |
| *C12Q 1/689* | (2018.01) |
| *C02F 3/00* | (2006.01) |
| *C12Q 1/6809* | (2018.01) |

(52) U.S. Cl.
CPC ........... *C02F 3/2893* (2013.01); *C02F 3/006* (2013.01); *C02F 3/28* (2013.01); *C02F 3/308* (2013.01); *C02F 3/341* (2013.01); *C12M 21/04* (2013.01); *C12N 1/20* (2013.01); *C12Q 1/689* (2013.01); *C12Q 1/6888* (2013.01); *C02F 2203/004* (2013.01); *C02F 2209/02* (2013.01); *C02F 2209/06* (2013.01); *C02F 2209/07* (2013.01); *C02F 2209/08* (2013.01); *C12Q 1/6809* (2013.01)

(58) Field of Classification Search
CPC ....... C02F 3/2893; C02F 3/341; C12M 21/04; C12N 1/20; C12Q 1/6888; C12Q 1/689; C12Q 1/6893; C12Q 1/6809
See application file for complete search history.

(56) References Cited

U.S. PATENT DOCUMENTS

| | | | | |
|---|---|---|---|---|
| 6,171,844 B1* | 1/2001 | Numata | ................... | A62D 3/02 435/252.1 |
| 2007/0178446 A1* | 8/2007 | Reeslev | ................... | C12Q 1/04 435/5 |
| 2013/0334131 A1* | 12/2013 | Allen | ..................... | C02F 3/308 210/601 |
| 2016/0333348 A1* | 11/2016 | Clube | ............... | A61K 31/7105 |

OTHER PUBLICATIONS

W. Ahmed et al., Toolbox Approaches Using Molecular Markers and 16S rRNA Gene Amplicon Data Sets for Identification of Fecal Pollution in Surface Water, Applied and Environmental Microbiology, https://aem.asm.org/content/81/20/7067/article-info, Sep. 22, 2015.
Eric A. Dubinsky et al., Microbial source tracking in impaired watersheds using PhyloChip and machine-learning classification, Water Research, vol. 105, pp. 56-64, Nov. 15, 2016.
Gregory R. Crocetti et al., Identification of Polyphosphate-Accumulating Organisms and Design of 16S rRNA-Directed Probes for Their Detection and Quantitation, Appl Environ Microbiol.; 66(3): 1175-1182, https://www.ncbi.nlm.nih.gov/pmc/articles/PMC91959/, Mar. 2000.
Tiago Palladino Delforno et al., Microbial diversity of a full-scale UASB reactor applied to poultry slaughterhouse wastewater treatment: integration of 16S rRNA gene amplicon and shotgun metagenomic sequencing, Microbiology Open, https://onlinelibrary.wiley.com/doi/full/10.1002/mbo3.443, Feb. 23, 2017.
Trevor Ghylin, Dissecting DNA: How DNA sequencing can solve foaming & filament issues, Water and Wastes Digest, Microbe Detectives, https://www.wwdmag.com/monitoring/dissecting-dna, Jan. 5, 2017.
Xiao-mei LV et al., Metagenomic Analysis of the Sludge Microbial Community in a Lab-Scale Denitrifying Phosphorus Removal Reactor, Applied Biochemistry and Biotechnology 175(7), Apr. 2015.
Christopher M. Sales et al. Resource recovery from wastewater: application of meta-omics to phosphorus and carbon management, Current Opinion in Biotechnology, Current Opinion in Biotechnology, vol. 33, pp. 260-267, Jun. 2015.

(Continued)

*Primary Examiner* — David C Thomas
(74) *Attorney, Agent, or Firm* — Husch Blackwell LLP

(57) ABSTRACT

A method is described for recovering resources from a microbe supporting environment such as a water treatment system, comprising the steps of using microbial DNA sequencing to analyze the microbiome of the microbe supporting environment and identifying adjustments to the microbial content of the microbiome that will be useful in extracting resources from the microbe supporting environment such as a water treatment system, wherein the resources extracted can include, for example, methane released by microbes, nitrogen, phosphorus, or other contaminants generated by microbes, and/or clean water obtained by removing contaminants in a water treatment system.

20 Claims, 48 Drawing Sheets

(56) References Cited

OTHER PUBLICATIONS

Robert J. Seviour et al., The microbiology of biological phosphorus removal in activated sludge systems, FEMS Microbiology Reviews, vol. 27, Issue 1, pp. 99-127, https://academic.oup.com/femsre/article/27/1/99/500670, Apr. 2003.

Roland J. Siezen et al. Genomics of biological wastewater treatment, Microb Biotechnol.; 1(5):333-340, https://www.ncbi.nlm.nih.gov/pmc/articles/PMC3815239/, Sep. 2008.

BoonFei Tan et al., Next-generation sequencing (NGS) for assessment of microbial water quality: current progress, challenges, and future opportunities, Frontiers in Microbiology, , https://www.ncbi.nlm.nih.gov/pmc/articles/PMC4585245/, Sep. 25, 2015.

* cited by examiner

FIG. 7
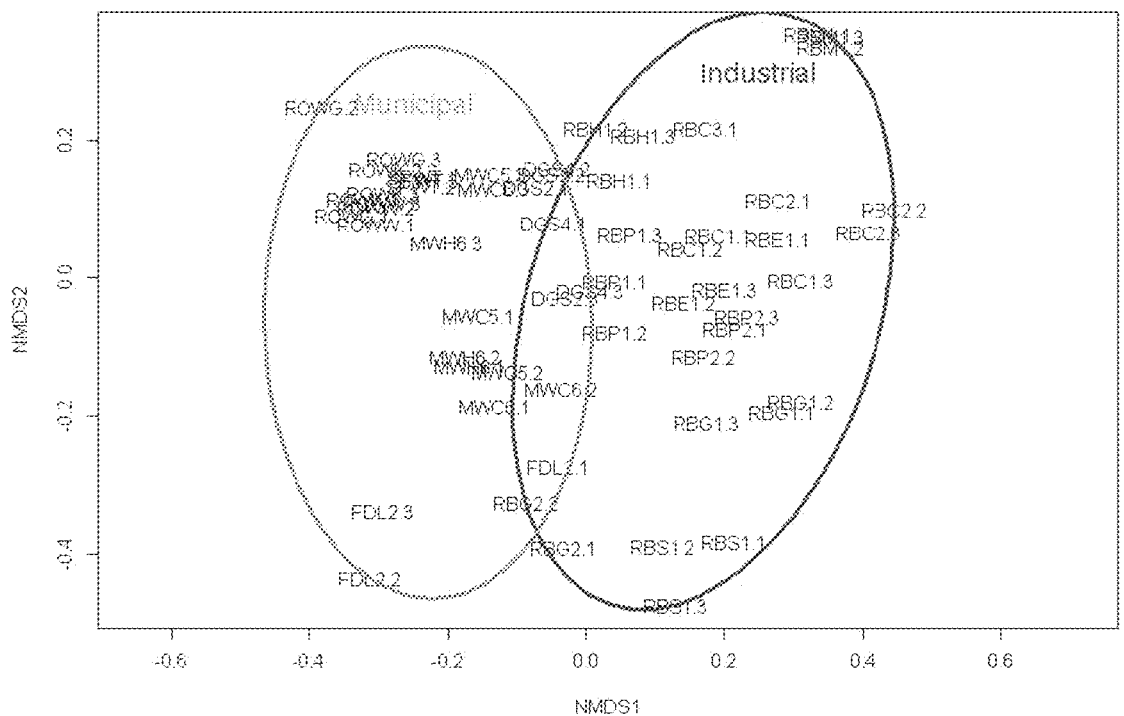
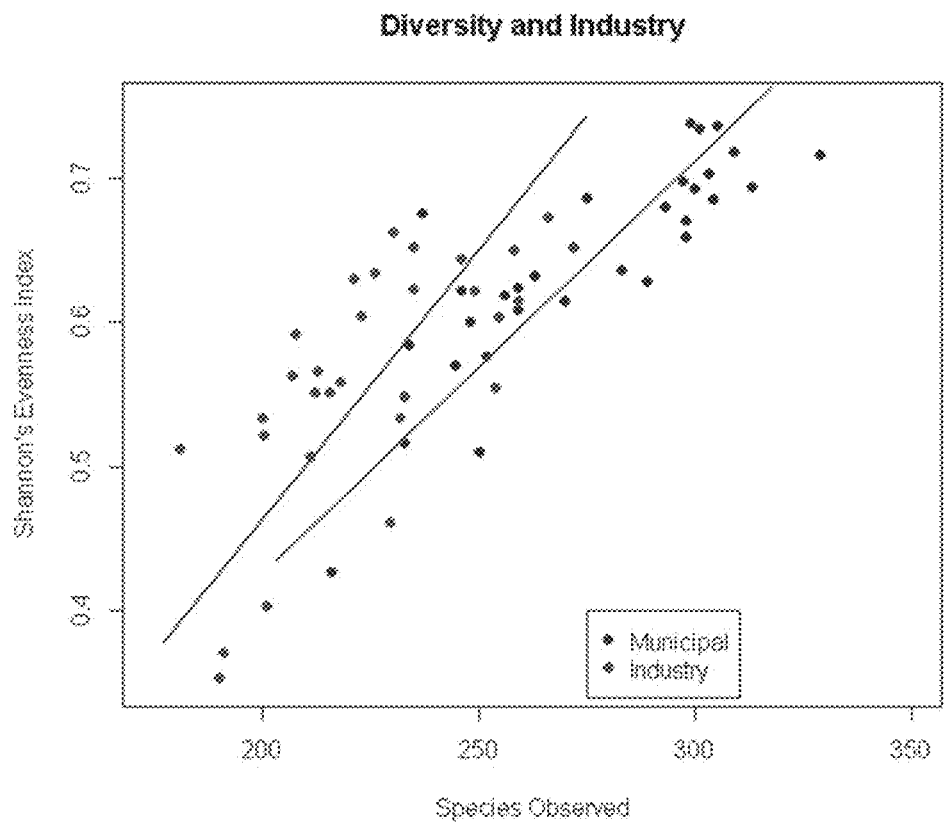
FIG. 8

Municipal (not significant)

Industrial (not significant)

Effect of pH and Temperature on Microbial Groups

Effect of pH and Temperature on Microbial Groups

METHOD OF USING MICROBIAL DNA SEQUENCING IN RECOVERING RENEWABLE RESOURCES FROM WASTEWATER AND OTHER WASTE STREAMS

CROSS-REFERENCE TO RELATED APPLICATIONS

This application claims priority to and benefit of application Ser. No. 62/501,857, filed May 5, 2017, and to application Ser. No. 15/961,776 and Ser. No. 15/961,816, both filed Apr. 24, 2018 and both of which also claim priority to applications Ser. No. 62/488,913 and Ser. No. 62/488,918, both filed Apr. 24, 2017, and to Ser. No. 62/501,857, all of which applications are hereby incorporated herein by reference in their entirety.

FIELD OF THE INVENTION

The present invention relates generally to a method of using microbial DNA sequencing in recovering resources from wastewater, and more particularly to recovering renewable resources such as, for example, energy, nutrients and/or clean water, and using microbial DNA sequencing with respect to identification, selection, development, and monitoring of probiotics in environmental factors.

BACKGROUND OF THE INVENTION

The present invention relates to a DNA-based method of identifying beneficial microbes (especially bacteria) for treatment of contaminated substances (especially polluted water such as wastewater). The identification of these beneficial bacteria is then used to isolate and enrich these bacteria to produce probiotics to improve and enhance remediation such as wastewater treatment.

The vast majority of probiotics sold for wastewater treatment (and other purposes) contain just a few different strains of bacteria. *Bacillus*-related bacteria are some of the most commonly used for probiotics for wastewater treatment and even for human gut health. These bacteria have been used as probiotics not because they have been proven to provide tangible benefit but rather because they are easy to grow and turn into a product because they survive well in dry spore form. A probiotic can include one or more microorganisms that can have a beneficial effect on a system, such as a water system or wastewater system or the like.

Many studies have shown that the human gut contains little to no *Lactobacillus*, even if a person is actively taking it as a probiotic. Likewise, similar studies in wastewater treatment plants have shown that the vast majority of microbes coming into a plant from the sewer do not survive in the treatment plant and the microbiome in the plant has little semblance to the microbiome in the sewage. Additionally, studies have shown that *Bacillus* is relatively uncommon in wastewater treatment plants as it appears not to be a conducive environment to its growth. Additionally, studies have shown that adding *Bacillus* (which is the most common probiotic available commercially) does not impact the process beneficially and *Bacillus* is not detected in the system even while actively adding the probiotic. The microbiome is determined by environmental conditions (substrates, nutrients, temperature, solids retention time, biofilm presence, oxygen content, etc.) rather than the addition of probiotics.

Probiotics have some promise in the area of wastewater treatment, especially industrial wastewater treatment. Industrial wastewater treatment plants such as those at pulp and paper plants, oil and gas plants, food and beverage plants, etc., typically treat highly variable flows with unique compositions (such as, for example, phenols, methanol, etc.) that may only be degradable by certain types of microbes or by specific microbes. These plants also experience rapid environmental changes, shock loading, and toxicity that cause upsets and can require shutdown of the wastewater treatment plant which causes shutdown of the production facility, resulting in costs sometimes exceeding one million dollars. These upsets may kill some or most of the biomass in a system or they may provide an overload of wastewater which the existing amount of biomass is not sufficient to treat.

One potential method to alleviate a treatment plant upset is to add beneficial bacteria to quickly increase the active biomass and accelerate treatment and return to a steady state healthy condition.

The current industry method of adding *Bacillus* to help with these issues is likely not the most effective method since *Bacillus* does not typically live in these systems and is obviously not the microbe most adapted to consuming and degrading the compounds present in these waters.

As can be seen, there is a need for an improved method of identifying microbes that can provide beneficial impact in remediation systems and isolating, cultivating and transplanting these microbes.

SUMMARY OF THE INVENTION

One embodiment of the invention, described here by way of summary, is a method for recovering renewable resources such as (1) methane, (2) removed contaminants such as nitrogen or phosphorus, or (3) clean water from a wastewater treatment system by using microbial DNA sequencing to describe the microbial content of the microbiome of the wastewater treatment system, then identifying and/or recommending and/or making adjustments to the microbial content of the microbiome of the wastewater treatment system to target isolation and separation, through microbial action, of renewable resources desired to be recovered from the system.

Many resources, such as phosphorus, nitrogen, and methane, are typically obtained or refined from the ground or the earth. Because the earth is a finite resource, there is a need to find alternative sources for these, and other, materials. These materials are present in the waste products of many industrial, commercial, agricultural, and recreational activities, but there is a need for methods for efficiently recovering these materials from those waste streams.

Because these waste streams are constantly generated by so many different human activities, these waste streams provide a ubiquitous source of materials that is constantly being renewed. That is, these waste streams are constantly restored in numerous locations by normal human activities; these sources of recoverable materials will continue to replenish themselves and provide a reliable and renewable stream of recoverable resources. As the recovered resources are reused, more waste streams are generated, and each resource can be recovered and reused multiple times, amplifying the beneficial environmental impact created by the recovery of renewable resources.

The invention relates generally to the recovery of resources from wastewater, but is not limited to waste or water delivery systems. More broadly, the invention relates to a variety of waste streams, such as waste products generated by different industries including: pulp wastes generated from paper mills or cloth manufacturers, solid fermentation waste products left over after the production of foods and beverages, and biofuel waste products. The invention also relates to agricultural activities, including biological wastes generated by livestock or other animals, and to waste products associated with farming or agrarian efforts. The invention also relates to by-products from nonindustrial activities, such sewage transportation, food preparation, and water-based locations, such as water fountains, pools, lakes, and streams. This invention is suitable for processing the wastes or by-products generated by a number of industries and human activities.

These processed wastes or by-products can be in the form of a liquid, solid, semi-solid or sludge. The waste products can include microbes or bacteria that can contribute to a biomass, compounds usable as nutrients by microbes, contaminants, and components suitable for recovery. Microbial-based DNA sequencing can be used to optimize different waste streams into viable resource recovery systems.

More broadly the invention relates to recovery of resources from any microbe supporting environment. A water treatment system is one example of such a microbe supporting environment, but other environments which support microbes and from which it may be desirable to recover resources are also within the scope of an embodiment of the invention.

Resources recoverable can include methane, which can be released by microbes in the system and is useful as a source of energy. Resources recoverable can include nitrogen or phosphorus, which are useful as agricultural fertilizers but are found as contaminants in wastewater treatment systems and/or waste streams. By identifying and appropriately adjusting the microbial content of a wastewater treatment system, such contaminants can be reclaimed and reused. Another example of a recoverable resource is producing clean water from wastewater using microbes to facilitate the process. Additionally, a further objective and benefit of an embodiment of the inventions is that controlling microbe populations in biofilms can be important and beneficial for clean water production using membrane processes which are prone to biofouling.

The recovery of renewable resources from waste systems can be optimized by improving the design of the recovery system, improving the operation of the recovery system, or by treating the system to run with greater efficiency or efficacy. At least one embodiment of the invention calls for taking multiple samples from multiple locations. Another embodiment calls for taking multiple samples over time, and using the repeated analyses to monitor the recovery system. Thus, a user can continuously monitor the system to ensure optimal activity, identify sub-optimal activity and determine its cause, and monitor the system to gauge the system's response to the user's efforts at optimization of the system.

These features enable the user to engage in precision editing of the microbiome, to modify the microbial system to preferentially support specific microbes or microbes with particular activities (e.g., methanogens). It enables a user to achieve an optimal balance of microbes for specific recovery efforts. These features also enable a user to track the success or failure of efforts to achieve an optimal balance of microbes, for any given operating parameter (for a given pH, feedstocks, chemicals, micronutrients), treatment process (e.g., filtration, addition of probiotics, etc.), recovery effort (e.g., phosphorus, nitrogen, clean water), or other need.

These features also enable a user to quantify and foster a diverse population of microbes. Diverse biomes are known to be resistant to a variety of environmental upsets or insults. While a particular environmental upset can wipe out a particular microbe or group of microbes that are vulnerable to that upset (such as, for example, heat, opportunistic pathogens, chemical contamination), a diverse population is likely to contain other microbes that are more durable and/or that can survive a particular environmental upset. Thus, a diverse biomass contains some microbes that will continue to survive and grow, ensuring the survival of the biomass, although likely with an altered composition. In comparison, if a biomass is made of only a few different microbes that are susceptible to the same environmental insult, then the occurrence of that particular insult can lead to the death of the biomass or allow the proliferation of undesired microbes (such as microbes that generate biofilms or foams or unpleasant odors).

Many industries are subject to regulations meant to reduce their consumption of certain resources such as energy, especially energy from non-renewable resources, and/or production of pollutants like carbon dioxide and/or other greenhouse gases. For example, "carbon credits" permit individuals or businesses to emit a certain amount of carbon dioxide, or burn a certain amount of fuel over a specified period of time. Carbon credits can be sold as a commodity, or purchased to offset one's own fuel-consuming activities. Carbon credits can be generated by the recovery of certain carbon-containing materials; for example, the recycling of methane generates significant amounts of carbon credits for use, sale, or trade. An aspect of the invention is to facilitate the generation of carbon credits, allowing a user to decrease the carbon credits required for operations or to generate carbon credits to sell or trade to others.

Similarly, Renewable Energy Certificates are tradable commodities that certify that a certain amount of energy was contributed to a shared energy system. Here too, methane provides high economic value for generating another kind of energy-based credit or commodity.

Another aspect of the invention is to facilitate the generation of energy, allowing as user to decrease its own energy consumption costs or to sell or trade energy as a commodity.

Other aspects of the invention relate to the recovery or scavenging of other recoverable resources for reuse, sale, or trade. In addition to generating substantial environmental benefits, the invention can also generate substantial economic value.

BRIEF DESCRIPTION OF THE DRAWINGS

The features of embodiments of the present invention which are believed to be novel are set forth with particularity in the appended claims. The drawings may not be to scale. The invention can best be understood by reference to the following description taken in conjunction with the accompanying drawings.

FIGS. 5A-5C are charts showing excerpts of analysis in a report producing results communicated in a microbiome digital signature report in accordance with one embodiment of the invention.

FIG. 7 is a visualization of microbial community similarities with municipal and industrial samples indicated with non-metric multidimensional scaling.

FIG. 8 depicts diversity and evenness for municipal and industrial samples.

DETAILED DESCRIPTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, one embodiment of the present invention provides a method of identifying, isolating, enriching and cultivating beneficial wastewater treatment microbes comprising the steps of:

collecting water samples from at least one location in a wastewater treatment system or large-scale wastewater treatment system;

filtering the water samples;

extracting DNA of microbes from the filters;

sequencing the DNA; and identifying the microbes comprising the DNA detected.

One embodiment of the present invention is able to identify microbes in the sample that are actually able to consume the unique compounds present in the wastewater One embodiment of the present invention includes the sensitive detection and identification of microbes (viable or not viable). There are various methods of doing this. The method of the present invention may include 16s PCR (Polymerase Chain Reaction) and DNA sequencing. Other methods may include DGGE (Denaturing Gradient Gel Electrophoresis), TRFLP (Terminal Restriction Fragment Length Polymorphisms), PCR, cloning and other equivalent or similar technologies and/or procedures as may be hereinafter developed. The present invention is intended to encompass all DNA-based technologies that detect and identify microbes for the purpose of identifying and cultivating beneficial microbes in wastewater treatment systems.

Figure 1:
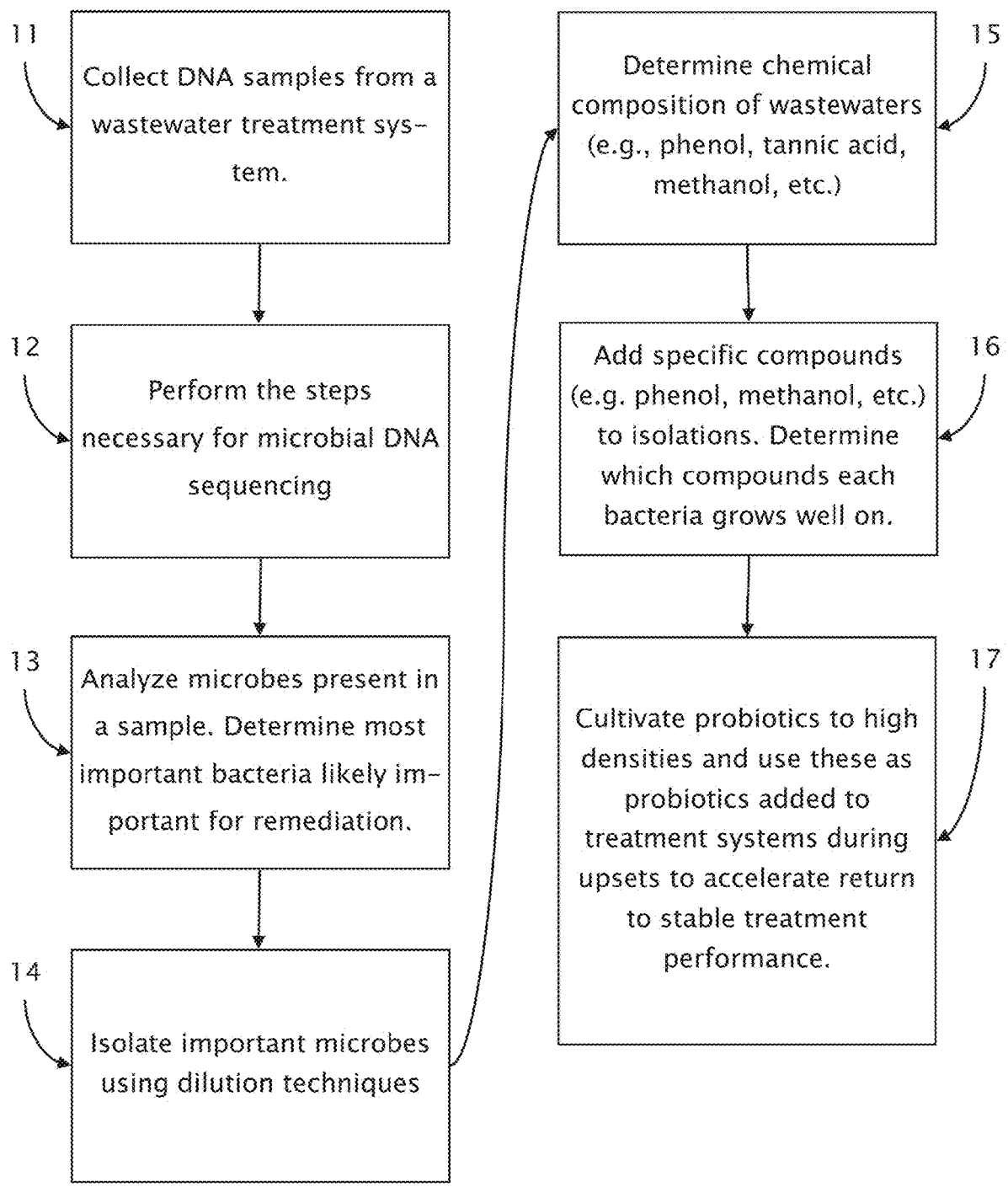
FIG. 1 is a flowchart illustrating the steps in a process in accordance with an embodiment of the invention.

Referring now to FIG. 1, an embodiment the present invention may include the following steps, as depicted in the flow chart. A collecting step (11) in which one can or will collect DNA samples from a wastewater treatment system. A sequencing step (12) in which one can or will perform sub-steps necessary for microbial DNA sequencing. An analyzing step (13) in which one can or will analyze microbes present in sample and determine most abundant bacteria present likely to be important for remediation. An isolating step (14) in which one can or will isolate specific important microbes using dilution techniques. A chemical determining step (15) in which one can or will determine chemical composition of wastewaters (such as, for example, phenol, tannic acid, methanol, etc.). An adding step (16) in which one can or will add specific compounds (such as, for example phenol, methanol, etc.) to isolations of microbes and determine the compounds on which each bacteria grows well. A cultivating step (17) in which one can or will cultivate probiotics to high densities and use these as probiotics for adding to treatment systems during upsets to accelerate return to stable treatment performance. The cultivating step (17) can result in the amplification of the number of one or more microorganisms (preferably, one or more of the microbes isolated during the isolating step (14)), and the cultivated and amplified microorganisms are returned to the system as a probiotic treatment that confers a beneficial effect on the wastewater treatment system.

It should be understood, of course, that the foregoing relates to exemplary embodiments of the invention and that modifications may be made without departing from the spirit and scope of the invention as set forth in the following claims.

Referring now generally to FIG. 2 through FIG. 48, there is shown illustrations depicting an embodiment of the invention applicable in, for example, a microbiome study. Such a study can, in an embodiment, provide performance comparison of biogas anaerobic digesters using next generation DNA sequencing.

Figure 2:
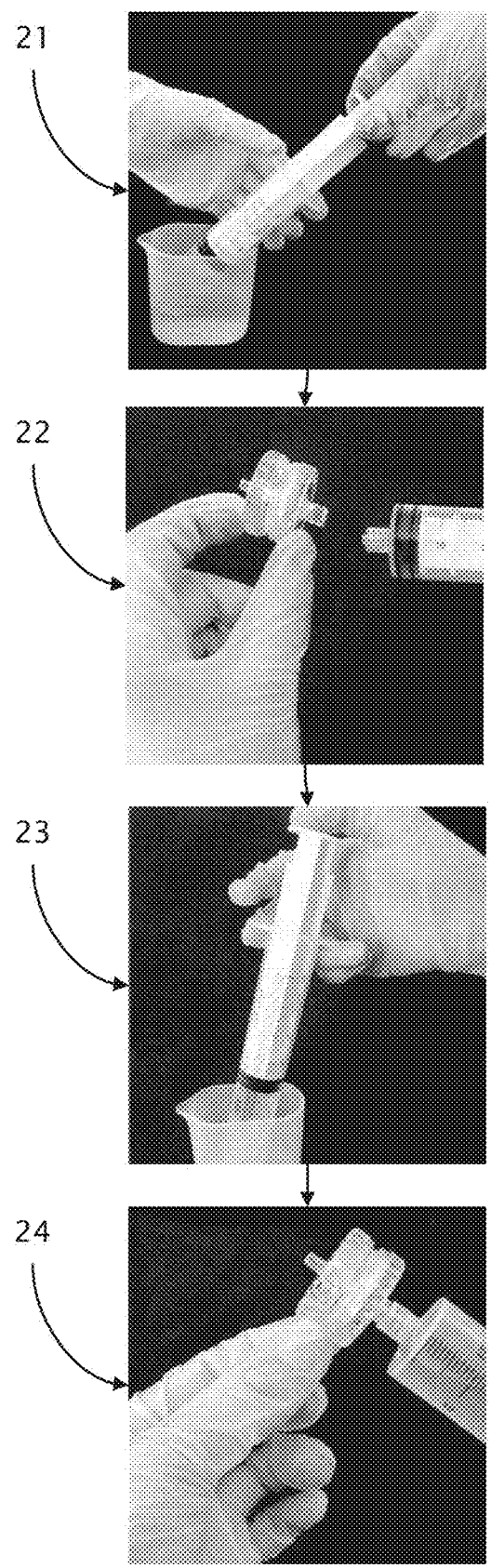
FIG. 2 illustrates the steps in a process of collecting samples in accordance with an aspect of one embodiment of the invention.

Referring now to FIG. 2, there is shown the steps of collecting a representative sample. Preferably, the person collecting the representative sample can wear gloves to prevent, avoid, or reduce contamination of the collected sample. The process as shown in FIG. 2 and described illustrates collection of liquid samples. Those of ordinary skill in the art will appreciate that solids can also be collected with appropriate adjustments to the process such as, for example, including an appropriate desiccant and sealing the sample in an appropriate, preferably sterile, container such as, for example, those available commercially as WHIRL-PAK®. In a step (21) of one aspect of an embodiment, the collector can draw an amount of wastewater, preferably 1 ml. Alternatively, the collector may draw wastewater until back pressure is detected. Such back pressure can indicate clogging or overloading of the filter.

In a step (22) of one aspect of an embodiment, the collector can screw the filter housing on the syringe. In one aspect of an embodiment, the housing contains a filter to collect microbes.

In a step (23) of one aspect of an embodiment, the collector can push the syringe plunger to force the collected sample through the filter housing. The collector in one aspect of an embodiment will preferably stop forcing the sample through the filter if the collector detects back pressure indicating filter clogging. The collector in one aspect of an embodiment can further record the volume of the sample forced through the filter.

In a step (24) of one aspect of an embodiment, the collector can unscrew the filter housing from the syringe. The collector can in one aspect of an embodiment discard the syringe after the sample is collected and filtered. The collector can then preserve the integrity of the filter housing by not disassembling the filter housing, in order to avoid, reduce, minimize, and abate potential contamination of the sample.

An analysis and/or report in accordance with one embodiment of the invention can, in various embodiments, achieve a number of desirable objections. For example, one embodiment in accordance with the invention herein disclosed and described can be used in conducting a multi-client study focused on optimizing biogas anaerobic digesters at municipal and industrial wastewater treatment plants and agricultural and biomass systems. It is an objective of one embodiment to evaluate correlations between microbial community and operational data to link microbiome digital signature to anaerobic digester performance. It is an objective of one embodiment to digitize the microbiome of many different anaerobic digester systems across, for example, different facilities, climates, and times of year.

An analysis and/or report in accordance with an embodiment of the invention can be specialized for measuring and monitoring the ecology of Anaerobic Digester Systems at, for example, municipal and/or industrial wastewater treatment plants and/or agricultural and/or biomass systems for purpose such as optimizing, improving, or facilitating their performance. In an embodiment, certain desired microbes, such as all methane producing microbes listed in a suitable database can be identified, along with a quantification of percent prevalence. In an embodiment, other categories of microbes can be identified and quantified, include, for example, those known to be associated with generally disfavored activity such as, for example, hydrogenesis, fermentation/acetogenesis, methane consumption (typically aerobic), syntrophs, sulfate reducing bacteria (SRBs), and foaming. In one embodiment, communication concerning such analysis can include the DNA sequencing results of each sample, grouped and analyzed for each digester included in the study, and each digester type. In an example of such an embodiment, survey data can be included to augment, illustrate, and further specify DNA testing. In an embodiment, communication concerning such analysis can also include identification of the top ten microbes based on percent prevalence. In an embodiment, in addition, many other microbes important in wastewater treatment can further be identified. In an embodiment, a complete listing of all microbes identified can be provided.

Information regarding the microbiome may be determined by an analysis done in accordance with an embodiment of the present invention. The information having been determined in such a manner may then be communicated in a Microbiome Digital Signature (MDS) report. An MDS report can create actionable insight, regarding the composition of the biome and possibilities for adjusting the biome to recapture resources therefrom.

Figure 3:
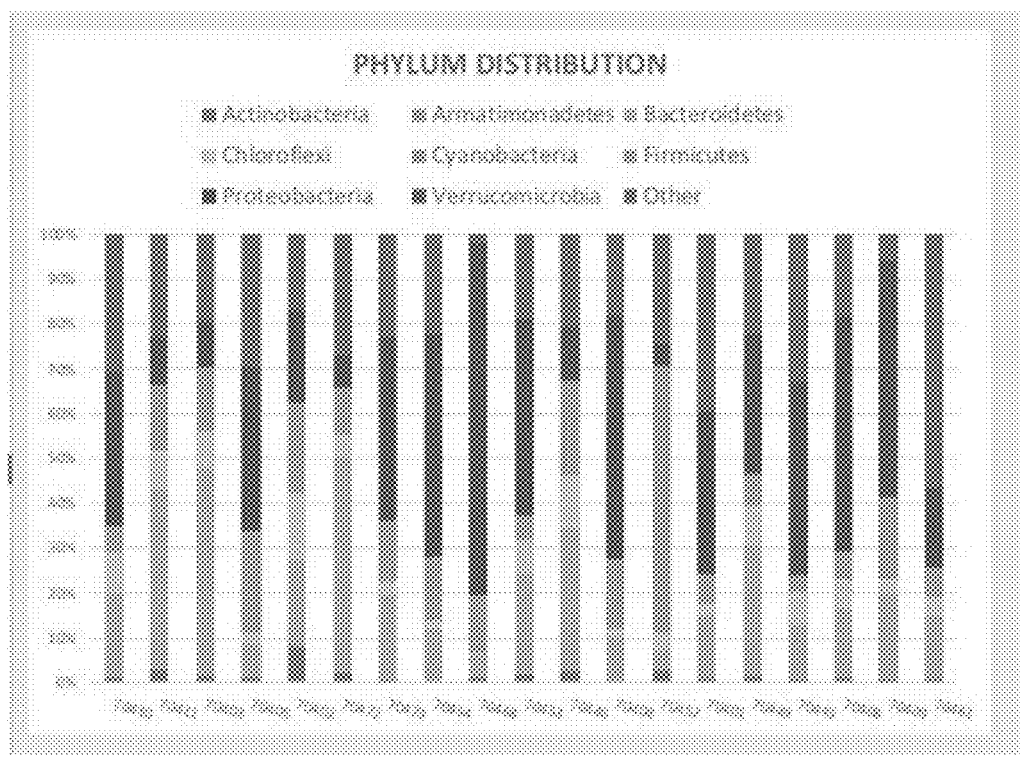
FIG. 3 is a chart showing phylum distribution results communicated in a microbiome digital signature report concerning anaerobic digesters in accordance with one embodiment of the invention.

Referring now to FIG. 3, there is illustrated an example of information regarding phylum distribution for anaerobic digester microbes. Such information may be included in an MDS report. The example shown communicated information regarding the distribution of Actinobacteria, Armatimondates, Bacteriodetes, Chloroflexi Cyanobacteria, Firmicutes, Proteobacteria, Verrucomicrobia, and other phylums. As further illustrated in FIG. 3, labels on the horizontal axis contain identifiers for particular samples, which may be referenced to time and place of collection for said samples. The vertical axis for each bar indicates the percentage composition of each phylum for the particular identified sample.

Figure 4:
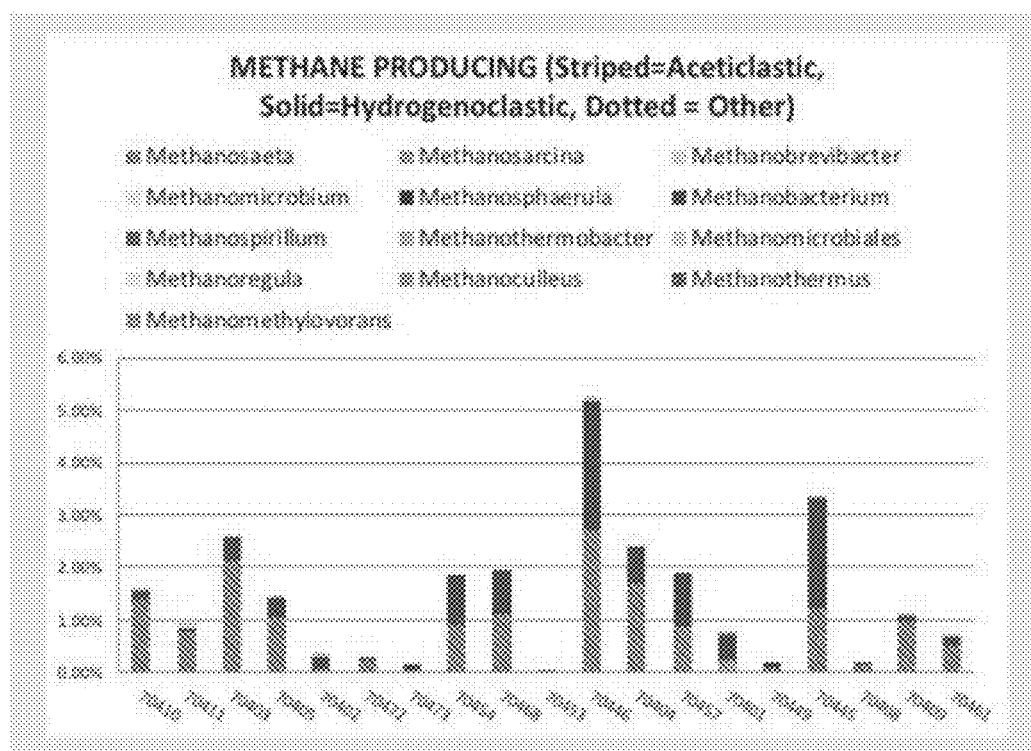
FIG. 4 is a chart showing methane producing microbes communicated in a microbiome digital signature report concerning anaerobic digesters in accordance with one embodiment of the invention.

Referring now to FIG. 4, there is illustrated an example of information regarding in particular methane producing microbes for anaerobic digesters. Methane producing aspects of the microbiome can include aceticlastic, hydrogenoclastic, and other. Particular methane producing entities identified include *Methanosaeta*, *Methanosarcina*, *Methanobrevibacter*, *Methanomicrobium*, *Methanophaerula*, *Methanobacterium*, *Methanospirillum*, *Methanothermobacter*, *Methanomicrobiales*, *Methanoregula*, *Methanoculleus*, *Methanothermus*, and *Methanomethylovorans*. As further illustrated in FIG. 4, labels on the horizontal axis in contain identifiers for particular samples, which may be referenced to time and place of collection for said samples. The vertical axis for each bar indicates the percentage composition of each phylum for the particular identified sample. The vertical axis for each bar can indicate the percentage composition of each member for the particular identified sample. Note that because the methane producing members are not the entirety of the microbiome, the vertical bars indicate different percentages of methane producing members within the whole group.

Figure 5A:
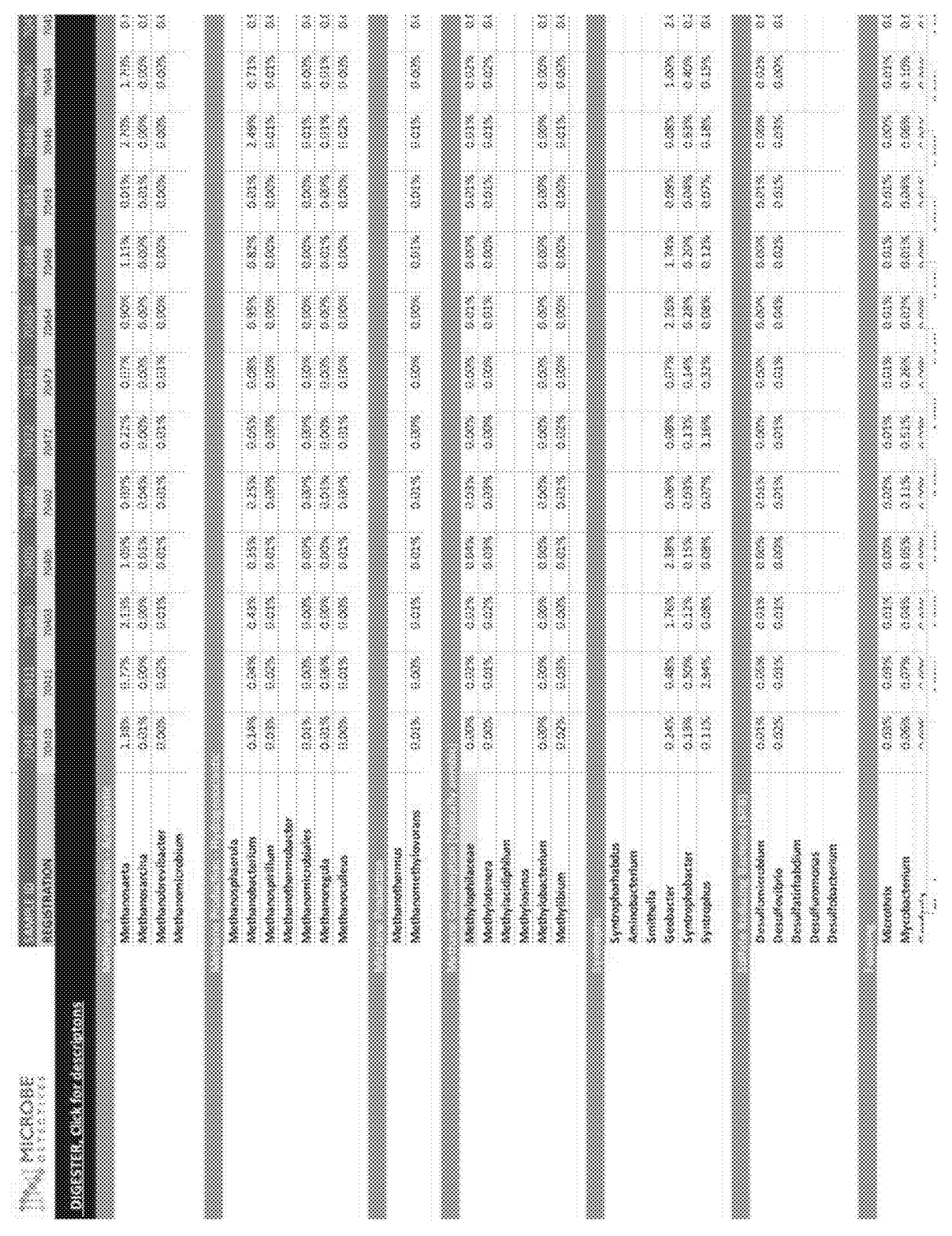
Figure 5B:
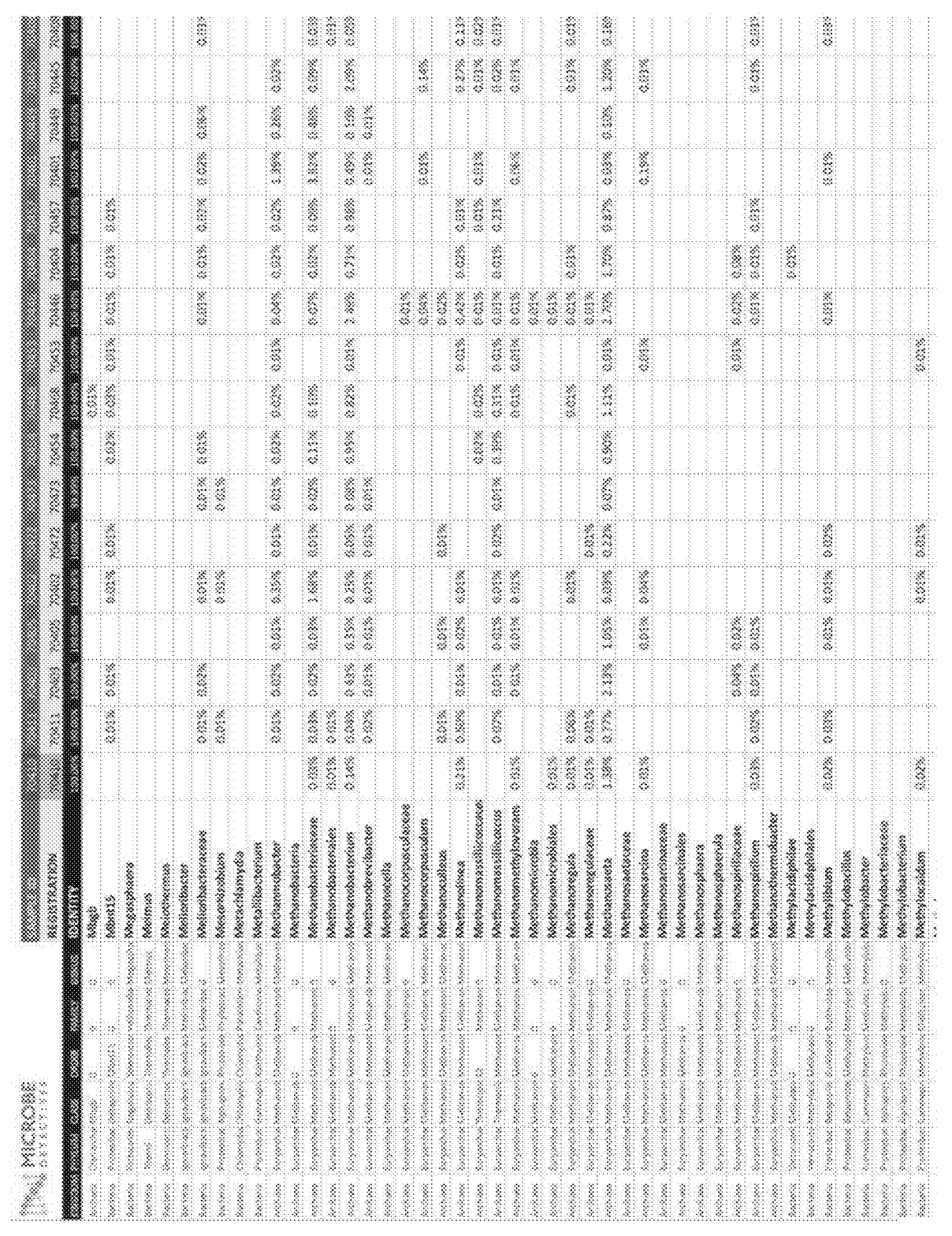

Referring now to FIGS. 5A-5C, there is illustrated an example of parts of a report providing a detailed analysis of the microbial composition of samples provided. FIG. 5A illustrates an excerpt of a report in accordance with an embodiment of the invention providing detailed analysis and information on categories of microbes of particular interest detected in samples such as, for example, methane producers, and, for example, microbes known to be associated with hydrogenesis, fermentation/acetogenesis, methane consumption (typically aerobic), syntrophs, sulfate reducing bacteria (SRBs), and foaming. FIG. 5B illustrates an excerpt of a report in accordance with an embodiment of the invention providing detailed analysis and information concerning a complete listing of all microbes identified. FIG. 5C illustrates an excerpt of a report in accordance with an embodiment of the invention providing detailed analysis and information concerning the top ten microbes based on percent prevalence as identified.

Anaerobic digestion is a microbial process that relies on the presence of many different types of microbes to work. The microbial community that makes up a specific digester's microbiome (the combination of all types of microbes in the digester) will be influenced by operational and design conditions, such as solids retention time, mixing, operating temperature and pH, feedstocks, and chemical addition. The microbial community in turn will affect digester outcomes such as chemical oxygen demand ("COD") removal and biogas production.

Anaerobic digesters are employed in wastewater and landfill systems worldwide to create renewable energy. An aspect of one embodiment of the invention is to facilitate analysis of the microbiome and operating performance of biogas anaerobic digesters. One objective of such an embodiment is to identify performance improvement opportunities resulting in greater energy production at a lower overall operational cost. Potential sectors for industrial applicability of such an embodiment include municipal, industrial, food processing, agricultural and landfills.

In one embodiment in accordance with the invention, next generation DNA sequencing and a specialized environmental microbiological database can be applied to identify bacteria and archaea in each digester sample. This can enable a community analysis to identify and quantify the relative abundance of microorganism types and how they change over time. This type of diagnostic insight is not possible with conventional testing methods such as microscopy, culture or quantitative polymerase chain reaction ("qPCR").

Anaerobic digestion and biogas formation generally rely on a complex community of microorganisms, including fermenters, methanogens, and sulfate-reducing bacteria. The performance of a digester depends on both operating conditions (such as, for example, influent organic load, operating pH, volatile fatty acid ("VFA") to alkalinity ratio) and the makeup of the microbial community present. A general objective of one embodiment of the invention is to aid a person in need of such information to characterize the link between digester operation and performance, and microbial community composition. A further objective of one embodiment is to characterize typical microbial communities present in digesters in different industries. A further objective of one embodiment is to identify key microbes and groups of microbes present in anaerobic digester across numerous industries. A further objective of one embodiment is to characterize the relationship between microbial community and operational conditions (such as, for example, including but not limited to, operating pH and organic loading). A further objective of one embodiment is to characterize the relationship between microbial community and digester outcomes (such as, for example, including but not limited to biogas production and composition and/or COD removal).

In accordance with one embodiment of the invention, a person in need of such analysis collects one or more, preferably one to three, biomass samples for each digester and completes an operational data survey. Operational data collected includes digester characteristics, chemical additives, temperature, pH, organic and solids loading, nutrients, VFAs, alkalinity, and biogas production and composition.

Digester biomass samples can be collected by filtering digester effluent through sterile filters, which are stored at a suitable temperature, preferably −20 degrees C. until shipment. In accordance with one embodiment, DNA is then extracted and 16S rRNA genes are amplified and sequenced using V4 primers and Illumina MiSeq technology. In other embodiments different sequencing technology may be employed. Following standard sequence processing steps, sequences are binned into related groups and classified by taxonomy.

In accordance with one embodiment, microbial community diversity is estimated by counting the number of species observed and calculating the Shannon's evenness index. Species observed indicates how many different types of microbes are present, while evenness indicates how evenly distributed their abundances are.

In accordance with one embodiment, correlations between two parameters can be tested statistically using linear models for input parameters that vary along a range (such as, for example, operating pH) and using a suitable statistical measure such as, for example, student's T-test for binary input parameters (such as, for example, whether a reactor is thermophilic or not). Multivariate ordination using non-metric multidimensional scaling ("NMDS") can be used to visualize differences in microbial community composition. A suitable statistical analysis package (such as, for example, the envfit function in the vegan package of R) can be used to evaluate the relationship between operating conditions and microbial community composition. Permutational multivariate analysis of variance (PERMANOVA) using Bray-Curtis distance calculations, or similar equivalent techniques, can further be used to evaluate which environmental parameters significantly correlated to microbial community composition.

Figure 6:
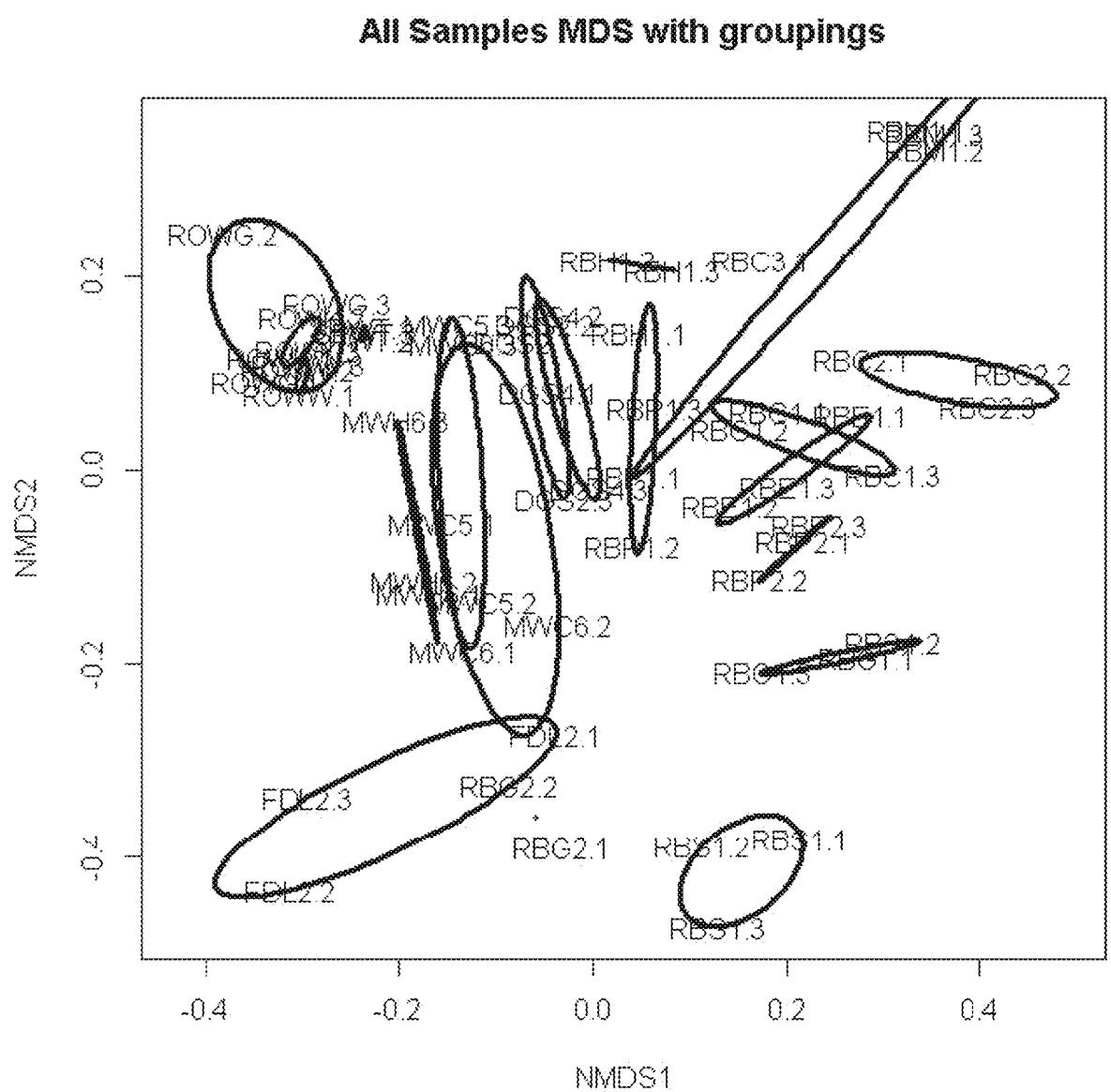
FIG. 6 is a visualization of microbial community similarities with each digester indicated using non-metric multidimensional scaling.

Referring now to FIG. 6, it can be seen that in one embodiment for each digester studied using the techniques in accordance with one embodiment of the present invention, microbial community composition is more similar to different dates from the same digester or municipality than to other digesters. Municipalities with more than one digester sampled appear grouped close together, which may suggest that digester feed characteristics have the largest effect on microbial community. For example, measurements from a digester designated "ROWG" tend to cluster together, as did measurements from the "MWC," "FDL," "RBM," and other digesters. This in turn may suggest that microbial community results are site-specific. The community composition associated with optimum results will vary between sites.

Referring now to FIG. 7, it can be seen that in one embodiment for each digester studied using the techniques in accordance with one embodiment of the present invention, microbial community composition differs significantly between municipal and industrial digesters. This may suggest that microbial communities in municipal and industrial settings are distinctly different.

Figure 18:
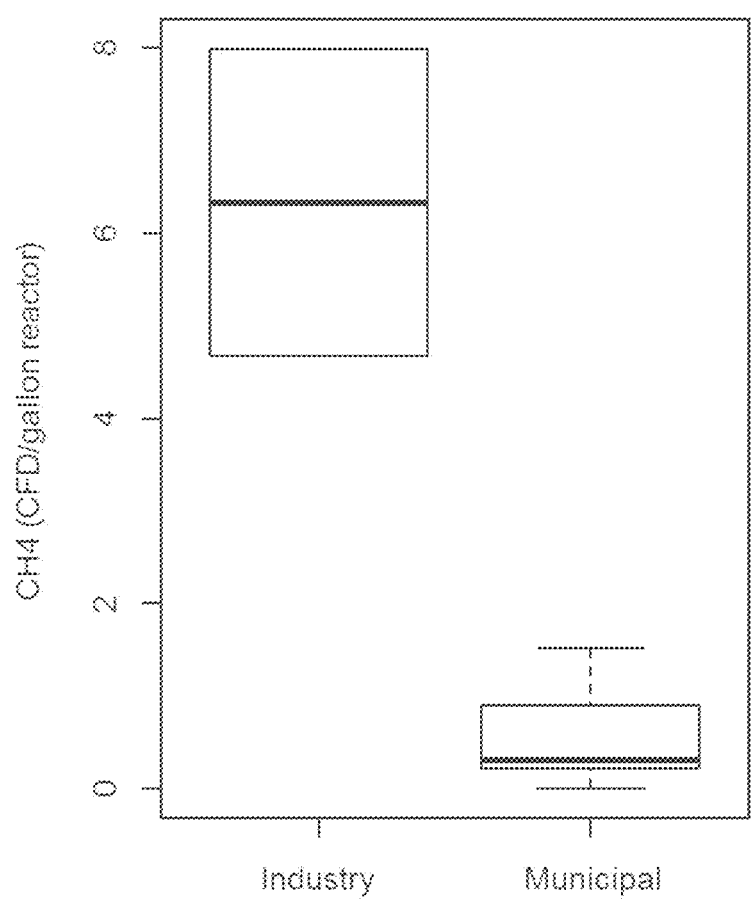
FIG. 18 is fifth example of a boxplot comparison of operating parameters and outcomes for industry vs. municipal.
Figure 19:
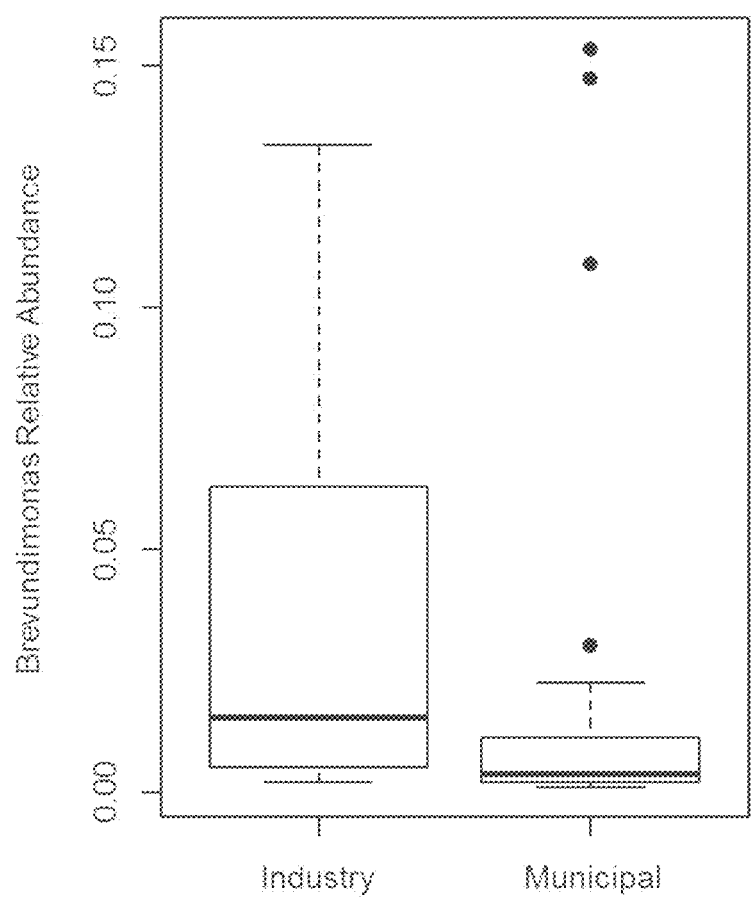
FIG. 19 is first example of a boxplot comparison of selected microbe groups for industry vs. municipal.
Figure 20:
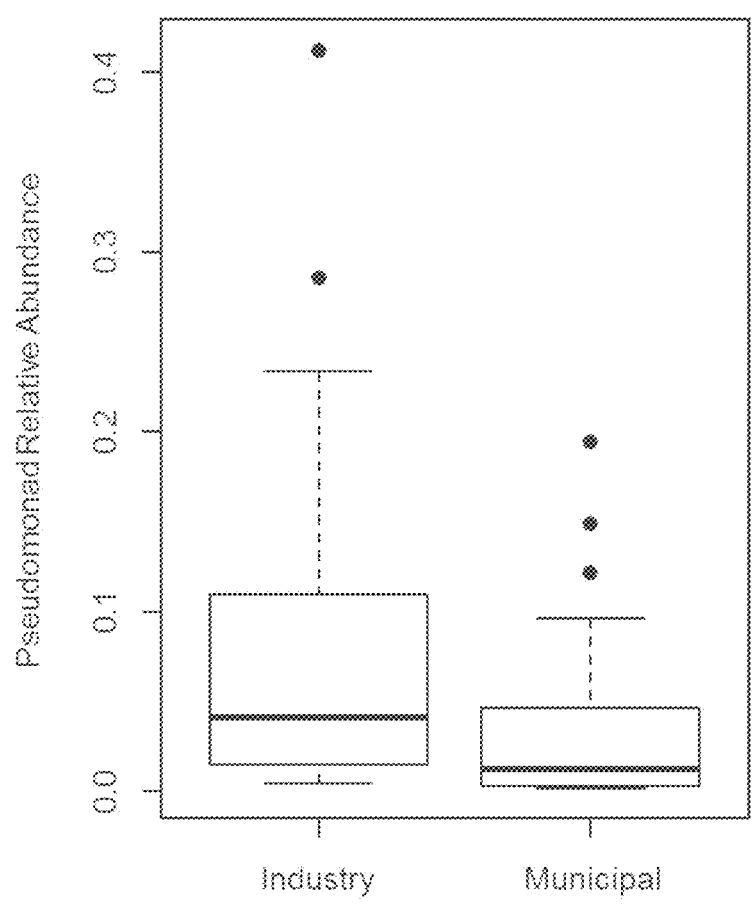
FIG. 20 is second example of a boxplot comparison of selected microbe groups for industry vs. municipal.
Figure 21:
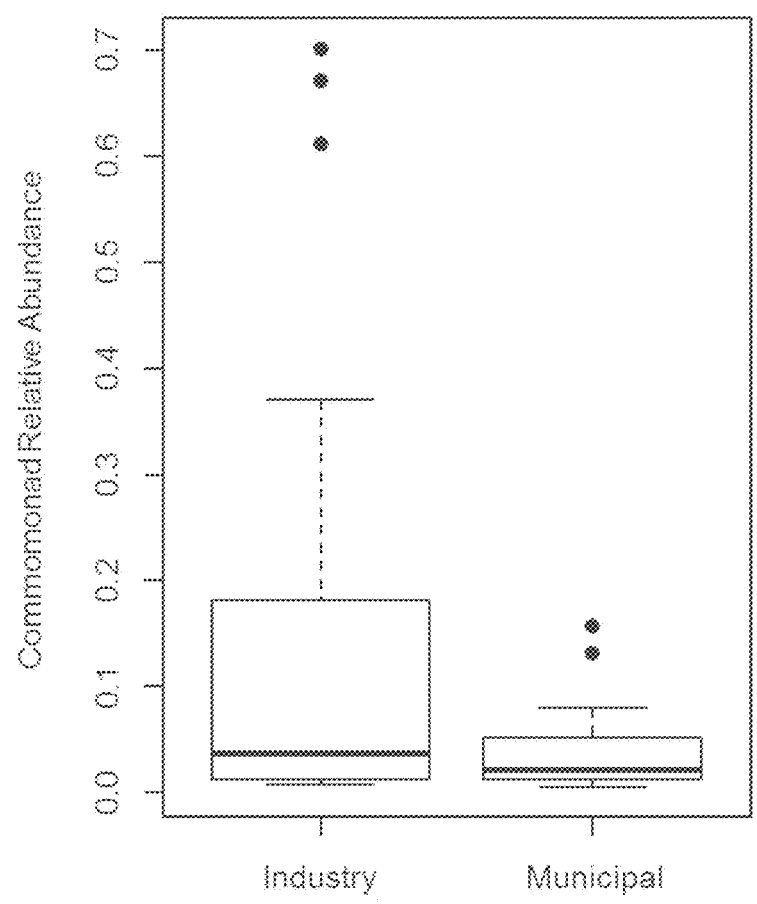
FIG. 21 is third example of a boxplot comparison of selected microbe groups for industry vs. municipal.

Referring now to FIG. 8, it can be seen that in one embodiment samples from industrial samples show significantly lower microbial diversity (p-value of 1E-7) (both species observed and evenness) and significantly higher archaea relative abundance (p-value of 0.005). More diversity (species observed) and evenness are present for municipal samples than industrial samples. FIG. 18 illustrates that industrial digesters also produced more methane per reactor volume than municipal digesters.

Figure 9:
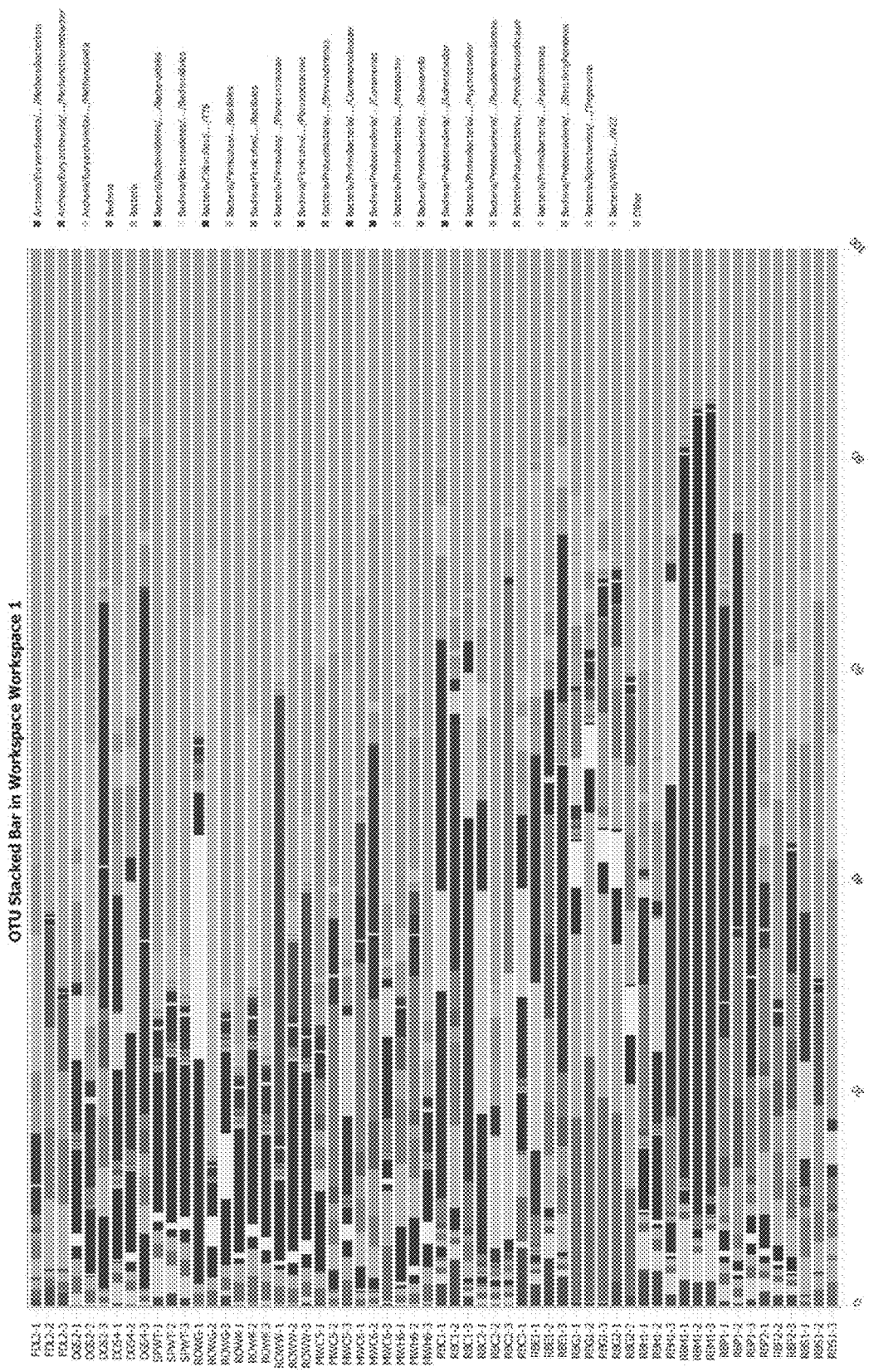
FIG. 9 depicts a summary of microbial community composition.

Referring now to FIG. 9, there is shown a chart prepared in accordance with one embodiment depicting all taxonomic units with greater than 1% abundance in the total data set, along with the three most abundant methanogen groups, which are all less than 1%. Each sample is shown along the vertical axis, with each microbial group indicated. The width of each bar reflects the relative abundance, or percent of the total community, for each microbial group. The bars on the right reflect the combinations other microbial groups that each made up less than 1% of the total data set; these were excluded for graphical clarity. Bacterial representatives of the phyla Firmicutes, Bacteroidetes, and Proteobacteria are the most abundant.

Methanogens produce methane from acetate or hydrogen. At present, methanogenesis can only be accomplished by archaea; no known bacteria can produce methane. Three primary methanogen groups were observed in this study: *Methanobacterium* spp., *Methanothermobacter* spp., and *Methanosaeta* spp. The first two are hydrogenotrophic, meaning that they get their energy from hydrogen produced by other microbes in the digester. *Methanosaeta* spp. is acetotrophic, meaning that it gets energy from organic acids, and typically dominates the methanogenic community at low acetate concentrations. *Methanothermacter* spp. prefers high temperatures and is primarily found in thermophilic reactors in this study. Generally, thermophilic reactors also have a higher ratio of *Methanobacterium* spp. to *Methanosaeta* spp., indicating that syntrophic hydrogen metabolism is more favorable at high temperatures.

Figure 11:
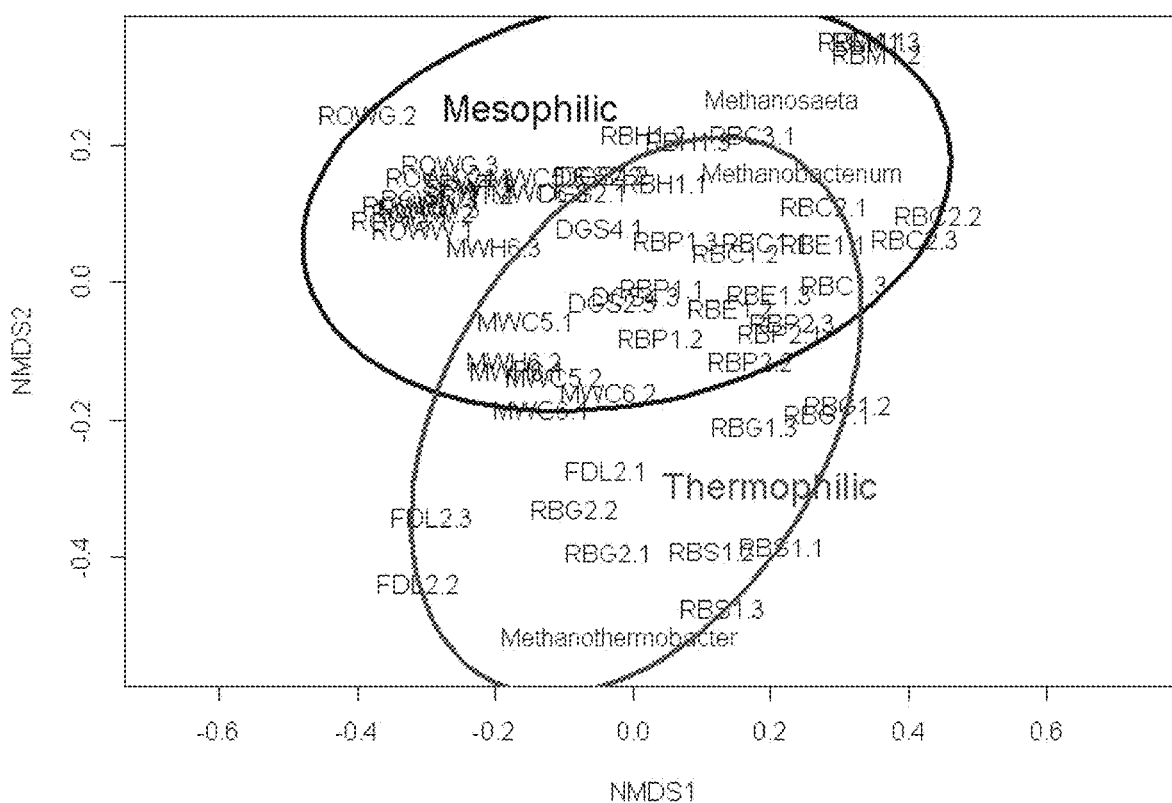
FIG. 11 is a visualization of microbial community similarities with mesophilic versus thermophilic reactors indicated and methanogen groups shown in blue with non-metric multidimensional scaling.

Referring now to FIG. 11, temperature also can have a significant effect on digester microbial community in general. Many microbial groups have an optimal temperature for growth, so mesophilic microbes may be expected to be more abundant in mesophilic reactors and similarly for thermophilic microbes in thermophilic reactors. Thermophilic reactors operate at higher temperatures than mesophilic reactors. Using NMDS analysis, FIG. 11 illustrates how mesophilic versus thermophilic reactors can group, and shows how different methanogen types can group with the different reactor types. This figure shows that mesophilic and thermophilic communities can be quite different, and that this trend is further reflected by the types of methanogens present.

Figure 12:
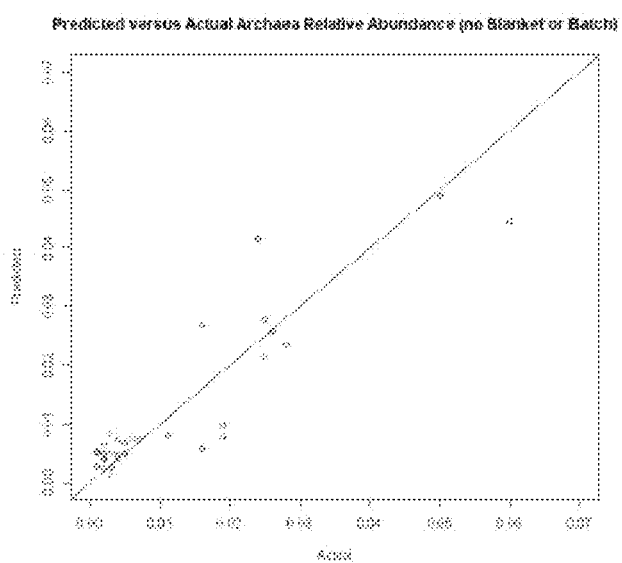
FIG. 12 depicts predicted versus actual percent archaeal abundance.

Referring now to FIG. 12, in accordance with one embodiment several multiple linear regressions can be analyzed for their ability to predict archaea relative abundance. Blanket and batch reactors can be excluded because they may have higher levels of archaea for unrelated reasons. FIG. 12 illustrates the actual relative abundance versus that predicted by a model, and shows how well the model fits the data. This correlation does not take into effect any other factors that affect archaeal abundance and does not necessarily reflect a causative relationship between pH, VFA: alkalinity ratio, and reactor operating temperature. In addition, the trend of higher archaeal relative abundance with both lower pH and higher VFA:alkalinity ratio is in conflict with typical operating wisdom. If pH gets too low and VFA:alkalinity gets too high, the reactor will sour and methanogenic archaea will not thrive. This conflict may be a result of the specific ranges of these values present in the study data set or may be the effect of other, unmeasured factors.

The results from such report in accordance with an embodiment of the invention can be used to develop several microbiome-based key performance indicators ("KPIs") that can be used by wastewater engineers and operators to inform the success of operation. These KPIs can reflect the health and composition of the digester microbial community that enables digester performance and can be used as targets for operation. For example, a bio-methane KPI can be based on the relative abundance of methanogens and may be weighted based on specific methanogen types. Another possible KPI can be reactor stability and resilience, assessed in accordance with the diversity and evenness of the digester microbiome. The bio-stability KPI can be based, for example, on community diversity and evenness. Other bases for KPIs can take into account how different a given microbial community is from that reactor's baseline community. Another possible KPI can be odor production. Odor production can be an important microbial outcome, as it affects nearby stakeholders and public perception. Most anaerobic digester odors result from production of reduced sulfur compounds, which is caused by sulfate-reducing bacteria.

Figure 13:
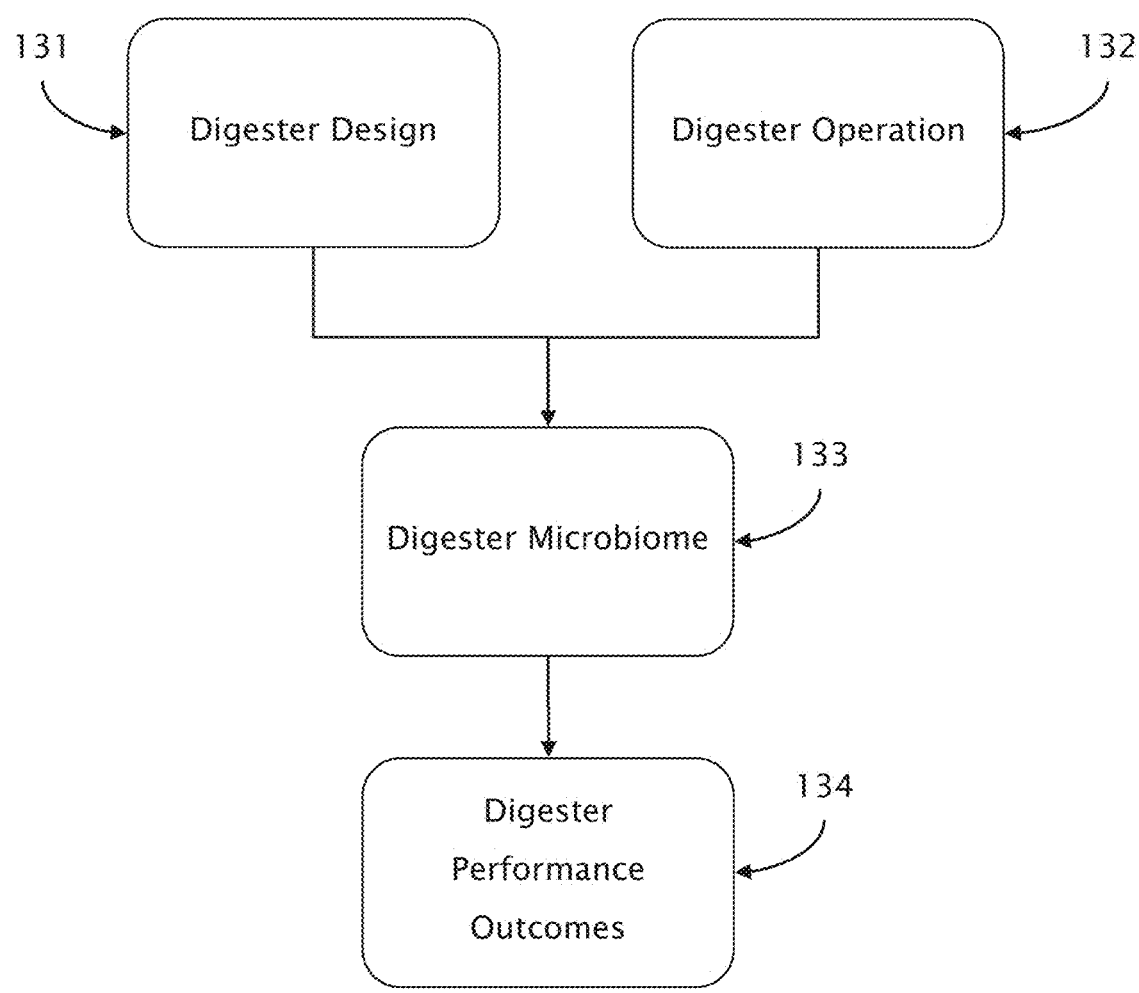
FIG. 13 depicts digester design, operations and performance as related to microbiome.
Figure 14:
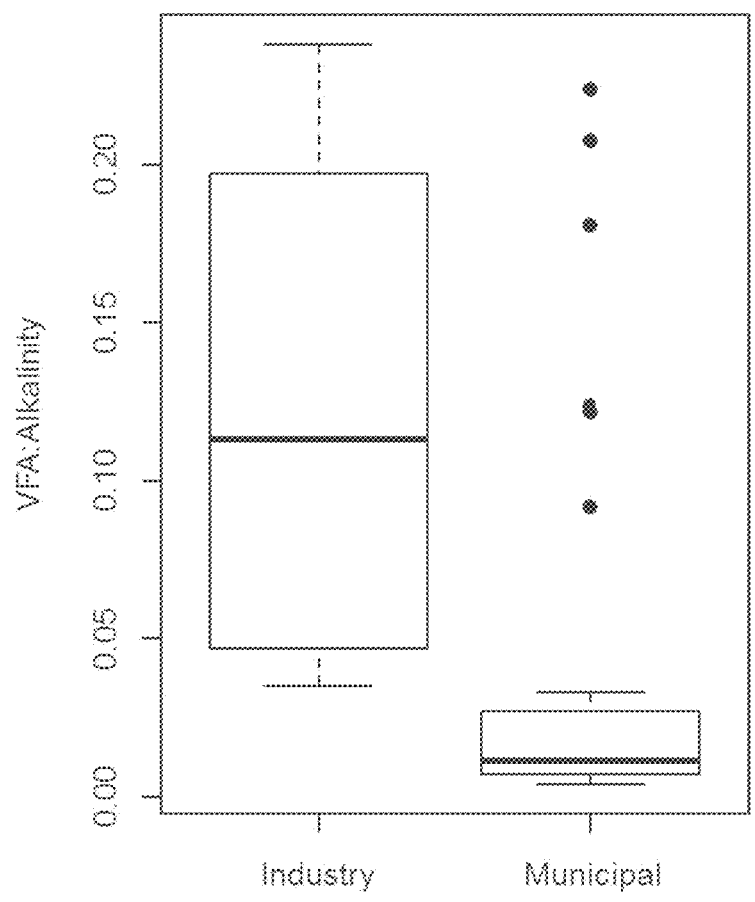
FIG. 14 is a first boxplot comparison of operating parameters and outcomes for industry vs. municipal.

Referring now to FIG. 13, there is depicted a flow diagram of system in accordance with one embodiment of the invention. The system depicted can represent, for example, an anaerobic digester. Embodiments can be used in a variety of areas of industrial applicability. As one example of such industrial applicability, an embodiment can be used in the context of a wastewater treatment facility. As another example of such industrial applicability, an embodiment can be used in treatment of a waste stream from a specific industry or agricultural site such as, for example, in treatment of stillage or slop as a byproduct left over from vat fermentation in a distillery process, or treatment of a waste stream from a paper or pulp plant, or treatment of a waste stream from agricultural runoff.

The system illustrated by FIG. 13, and the information derivable in the context of this system in accordance with an embodiment of the invention, has implications for digester performance and operation. The results from reports such as, for example, the reports described and depicted above can be used to develop several microbiome-based Key Performance Indicators (KPIs) that can be used by, for example, in one embodiment, wastewater engineers and operators to inform the success of operation. In another embodiment, stillage treatment engineers and operators can use KPIs determined in accordance with that process to inform the success of that operation. These KPIs reflect the health and composition of the digester microbial community that enables digester performance and can be used as targets for operation.

Examples of KPIs and their applicability within the digester operation and problem solving framework are described herein. Considerations relevant in Digester Design (131) can include, for example, solids retention time (SRT), hydraulic retention time (HRT), reactor type, and whether or to what extent it is mesophilic/thermophilic. The SRT is the average time that bacteria (solids) are in the anaerobic digester. The HRT is the time that the wastewater or sludge is in the anaerobic digester. Considerations relevant in Digester Operation (132) can include, for example, operating pH, operating temperature, feedstocks, COD, nutrient loading, chemical additions, VFA:alkalinity, and mixing. Considerations relevant in Digester Performance Outcome (134) can include, for example, biogas production, COD removal, VSS destruction, odor, and others.

These considerations and other similar considerations in an anaerobic digester can affect and/or be affected by the state of the Digester Microbiome (133). In accordance with one embodiment of the invention, the state of the Digester Microbiome (133) can be described, quantified, measured, and/or assessed with KPIs, selected in accordance with the particular anaerobic digester process implemented. KPIs can include, for example, bio-methane KPIs, bio-stability KPIs, and/or bio-odor KPIs.

Taken together, the Digester Microbiome (133), as monitored, analyzed, and/or examined in accordance with an embodiment of this invention, and Digester Performance Outcomes (134) can provide a plurality and variety of performance metrics. The considerations discussed above concerning Digester Operation (132) require accurate and continuous monitoring of operations. The performance metrics described above with respect to the Digester Microbiome (133) and the Digester Performance Outcomes (134) can inform the selection, manipulation, and adjustment of considerations affecting Digester Operation (132). Additionally, performance metrics described above with respect to the Digester Microbiome (133) and the Digester Performance Outcomes (134) can inform the selection, arrangement, planning, maintenance, and updating of Digester Design (131).

Figure 10:
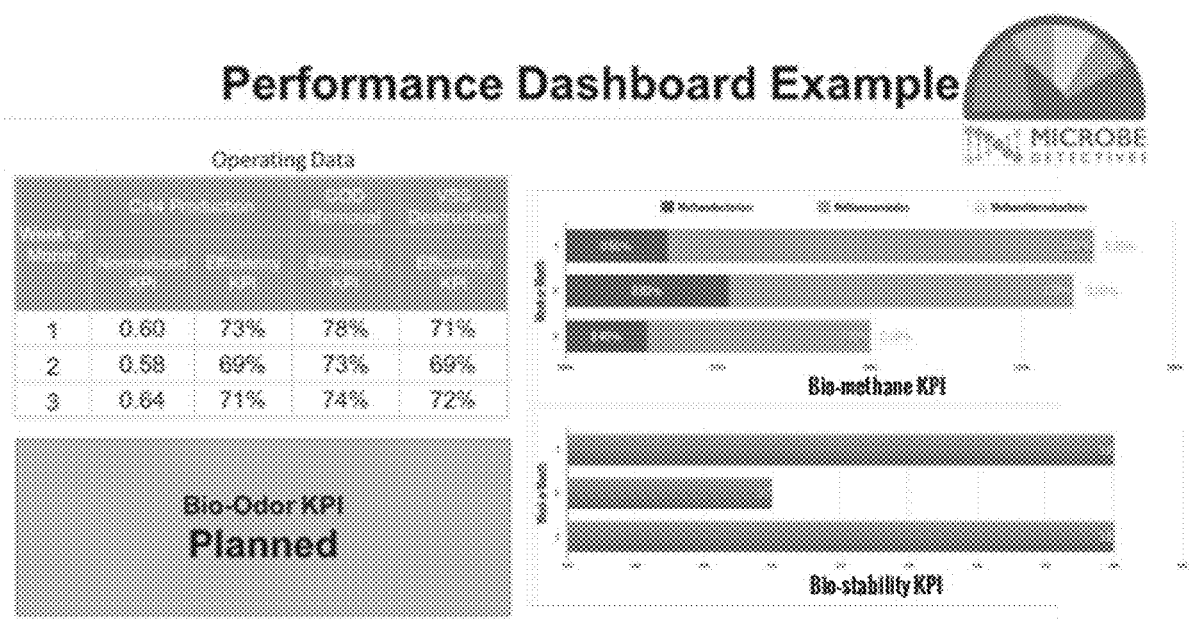
FIG. 10 depicts an example of a Microbe Detectives digester dashboard in accordance with an aspect of one embodiment of the invention.

Referring now to FIG. 10, these in accordance with an embodiment of the invention, microbial community KPIs can be combined in a dashboard with KPIs such as, for example for reactor performance, including those for methane production, COD to methane conversion efficiency, COD removal, and volatile suspended solids ("VSS") destruction. An objective of one embodiment of the invention is to be a tool for operators to compare reactor performance to microbial community parameters over time and learn how the microbial community KPIs correlate to microbes and their performance in their system, which can in turn enable operators to use the microbial community KPIs as indicators of reactor health and to better understand what range of conditions they should target for each.

In accordance with one embodiment, digester biomass samples can be collected by wastewater operators and filtered through a filter, such as a 0.45 µm, DNA-free syringe filter. The filter can be stored at suitable conditions, preferably at a temperature of −20 degrees C., until processing. DNA can be extracted from the filters using an appropriate kit.

The 16S rRNA gene V4 variable region PCR primers 515/806 with barcode on the forward primer can be used in a 30 cycle PCR (5 cycle used on PCR products) using an appropriate kit under proper conditions such as, for example, the following conditions: 94° C. for 3 minutes, followed by 28 cycles of 94° C. for 30 seconds, 53° C. for 40 seconds and 72° C. for 1 minute, after which a final elongation step at 72° C. for 5 minutes can be performed. After amplification, PCR products can be checked in 2% agarose gel to determine the success of amplification and the relative intensity of bands. Multiple samples can be pooled together in equal proportions based on their molecular weight and DNA concentrations. Pooled samples can be purified using calibrated beads. Then the pooled and purified PCR product can be used to prepare a DNA library by following an appropriate DNA library preparation protocol. Sequencing can be performed on a suitable sequencer following the manufacturer's guidelines.

Sequences can be depleted of barcodes and primers then short sequences <200 bp can be removed, sequences with ambiguous base calls removed, and sequences with homopolymer runs exceeding 6 bp removed. Sequences can then be denoised and Operational Taxonomic Units (OTUs) can be defined clustering at, for example, 3% divergence (97% similarity) followed by removal of singleton sequences and chimeras using an appropriate tool such as, for example, Uchime. Final OTUs can be taxonomically classified using an appropriate tool such as, for example, BLASTn against a curated database derived from sources such as, for example, GreenGenes, RDPII and NCBI.

In accordance with one embodiment, Alpha diversity metrics can be evaluated from the OTU table using 100 bootstraps. Multivariate ordination using NMDS can be used to visualize differences in microbial community composition. Singletons can be removed prior to ordination.

Correlations between two parameters can be tested statistically using linear models for input parameters that vary along a range (such as operating pH) and using a suitable test such as, for example, a student's T-test for binary input parameters (such as whether a reactor is thermophilic or not). At least two similar methods can be used to evaluate correlations between microbial community composition and operational and digester performance parameters: a.) permutational multivariate analysis of variance (PERMANOVA) using Bray-Curtis distance calculations using 100,000 bootstraps, and b.) the envfit function in the vegan package of R. Both methods identified the same parameters as significantly correlated to community composition: pH, VFA, VFA:Alkalinity, SRT, and temperature.

Referring now to FIGS. 14-48, there is depicted a variety of additional resources illustrating data analysis details.

In one embodiment in accordance with the present invention, information can be obtained in a multi-client biological nutrient removal ("BNR") study at municipal wastewater treatment facilities, focused on optimizing the programs of those facilities. An objective of one such embodiment is to enable and quantify substantial gains in BNR performance. An objective of one such embodiment is to apply DNA sequencing and operational data analyses to link microbiome digital signature to BNR performance. An objective of one such embodiment is to digitize the microbiome of many different BNR systems across different facilities, climates, and times of year.

In one embodiment in accordance with the invention, an objective is finding ways to remove phosphorus and nitrogen from the wastewater biologically instead of chemically, which results in a lower net resource consumption and also allows operators to recover phosphorus and nitrogen. Instead of chemically or mechanically treating for phosphorus and nitrogen, where phosphorus and nitrogen are removed from the water but have other environmental impacts (including, for example, the disposal of solid waste), such biological removal further allowing operators to concentrate those nutrients, collect them, and return them back into, for example, the fertilizer cycle. Biological nutrient removal can recover valuable renewable resources from the system and use less energy to treat water than conventional processes. In one embodiment in accordance with the invention, using metagenomics (the study of genetic material recovered directly from environmental samples) in wastewater treatment and resource recovery with metagenomic sequencing can suggest changes to operational strategy and sage hundreds of thousands of dollars.

DNA sequencing can help operators that are trying to do BNR in their plant finally see the bacteria that are useful for that process. Without DNA data it is difficult or even impossible to know exactly what is transpiring in a plant's ecology. One may, for example, observe phosphorus levels decreasing, but that observation does not indicate whether such decease is merely the result of biological uptake or whether, in the alternative, specific chemicals being used are affecting that outcome. With DNA data, in accordance with one embodiment of the invention, one can observe and identify biological phosphorus-metabolizing bacteria in the system. One can both ascertain the presence vel non of such bacteria and assess prevalence, and can track such populations over time. In a like manner, in one embodiment of the invention one can track other bacteria such as ammonia removers and denitrifying microbes.

Figure 15:
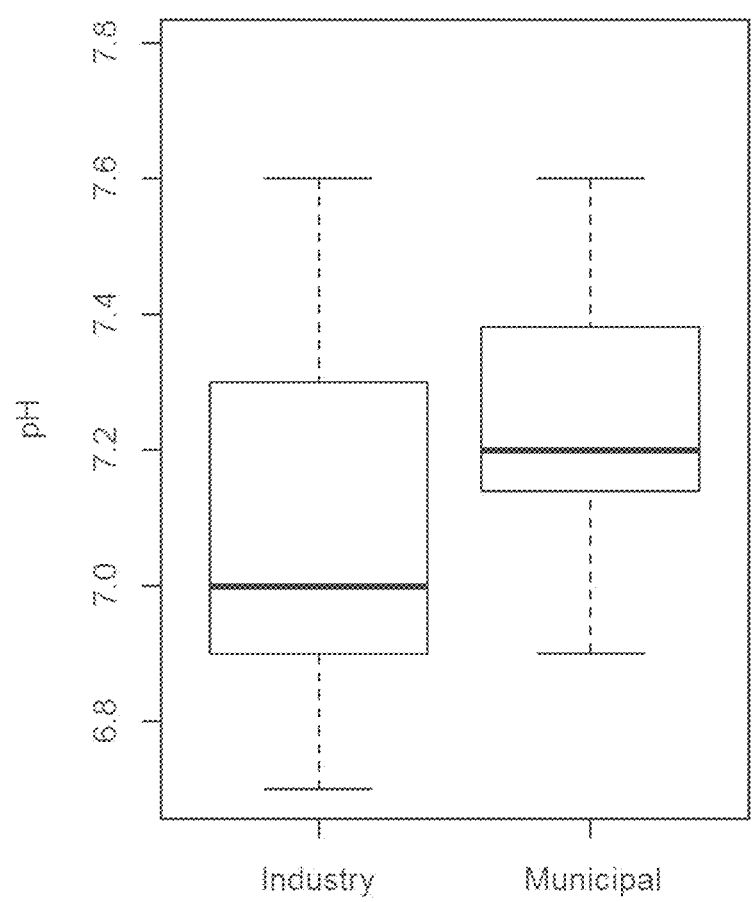
FIG. 15 is second example of a boxplot comparison of operating parameters and outcomes for industry vs. municipal.
Figure 16:
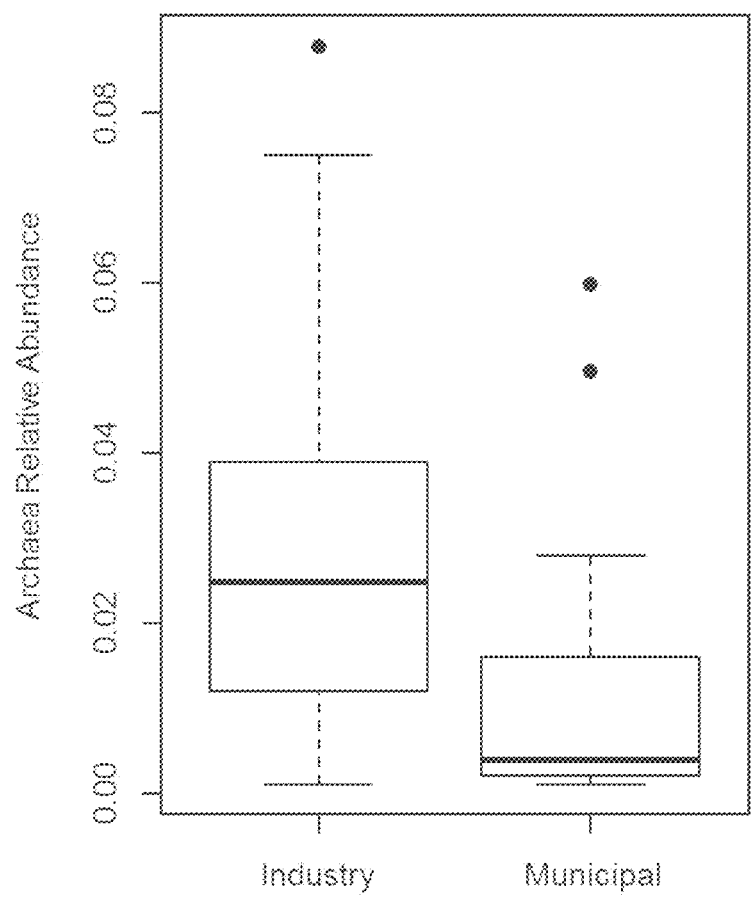
FIG. 16 is third example of a boxplot comparison of operating parameters and outcomes for industry vs. municipal.
Figure 17:
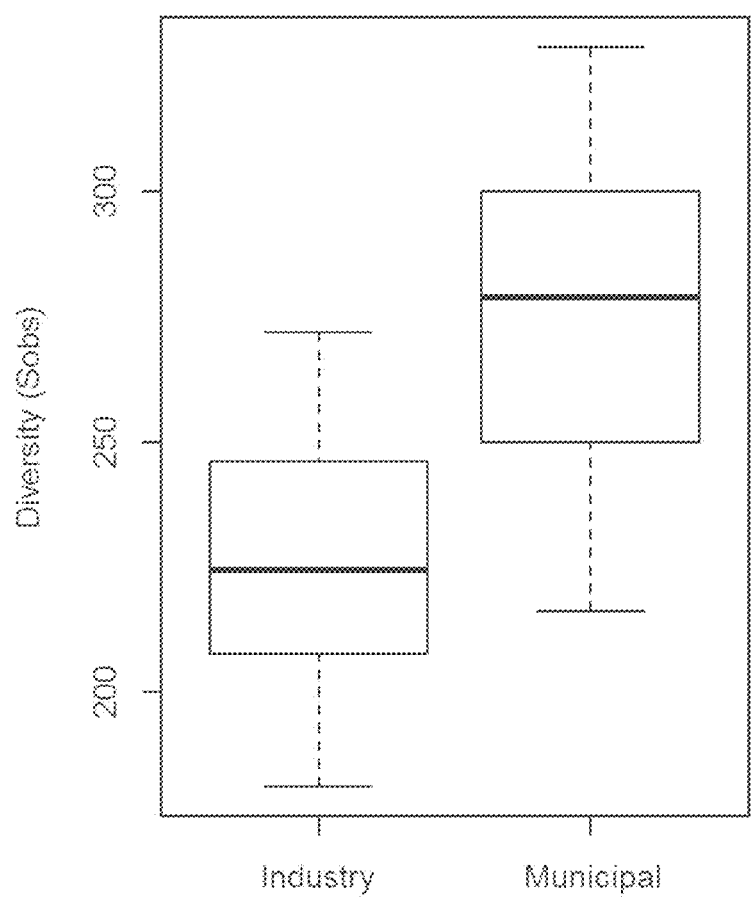
FIG. 17 is fourth example of a boxplot comparison of operating parameters and outcomes for industry vs. municipal.
Figure 22:
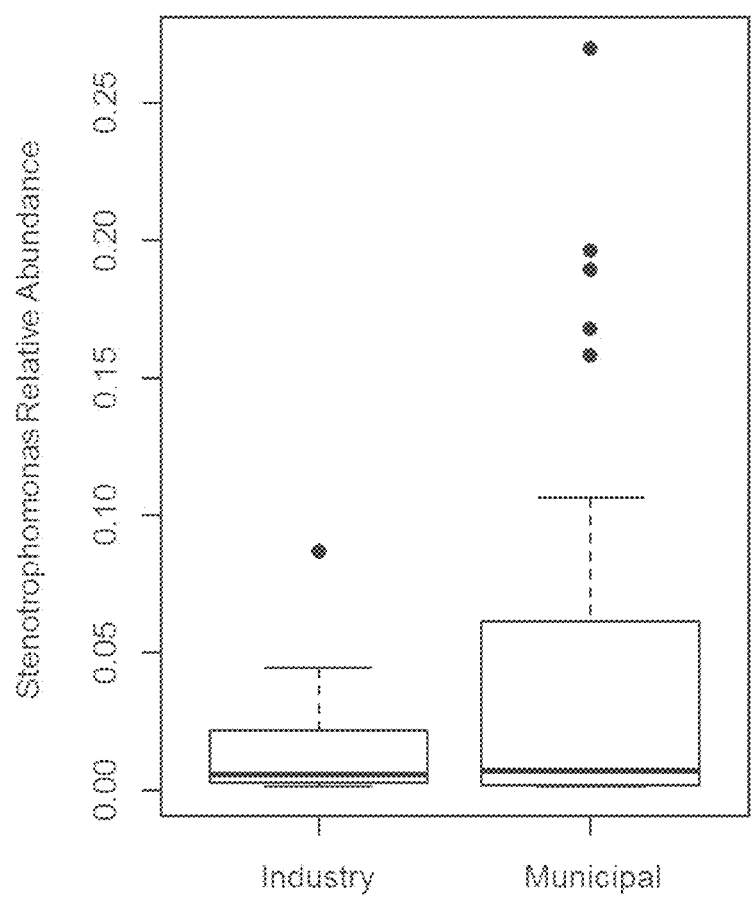
FIG. 22 is fourth example of a boxplot comparison of selected microbe groups for industry vs. municipal.

As shown in FIGS. 14-22, various chemical and biological aspects of industrial and municipal digesters are compared. Industrial and municipal digesters, as groups, exhibited measurably different chemical properties, including VFA:alkalinity (FIG. 14) and pH (FIG. 15). Differences between the two groups are also observed for certain microbiological parameters, such as Archea relative abundance (FIG. 16), overall microbial diversity (FIG. 17), and methane production (FIG. 18). In comparison, smaller differences are observed for parameters like *Brevundimonas* relative abundance (FIG. 19), *Pseudomonas* relative abundance (FIG. 20), *Commomonad* relative abundance (FIG. 21), and *Stenotrophomonas* relative abundance (FIG. 22).

Figure 23:
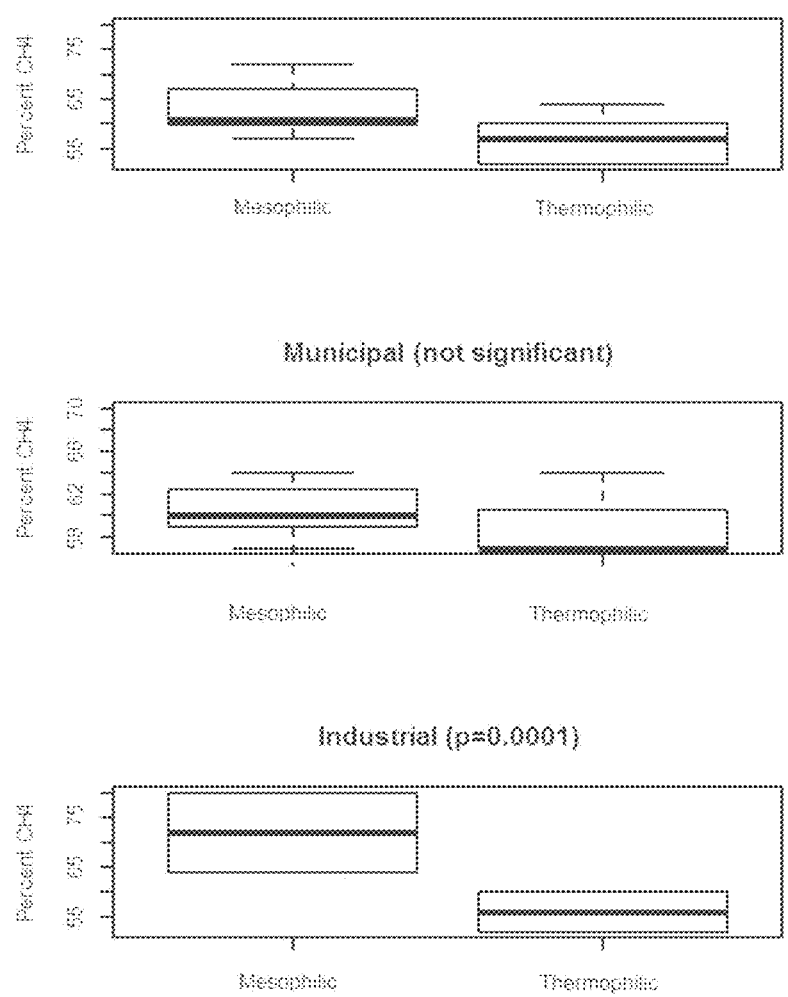
FIG. 23 is a first example of a boxplot depicting the effect of mesophilic/thermophilic for industry vs. municipal.

As shown in FIGS. 23-28, a variety of treatments are applied to digesters, and the effects of those treatments on to the recovery of different renewable resources are reported. As shown in FIG. 23, mesophilic digesters, having lower temperatures than thermophilic digesters, generally contain greater percentages of methane than do thermophilic digesters. This trend is reported in both municipal and industrial digesters.

Figure 24:
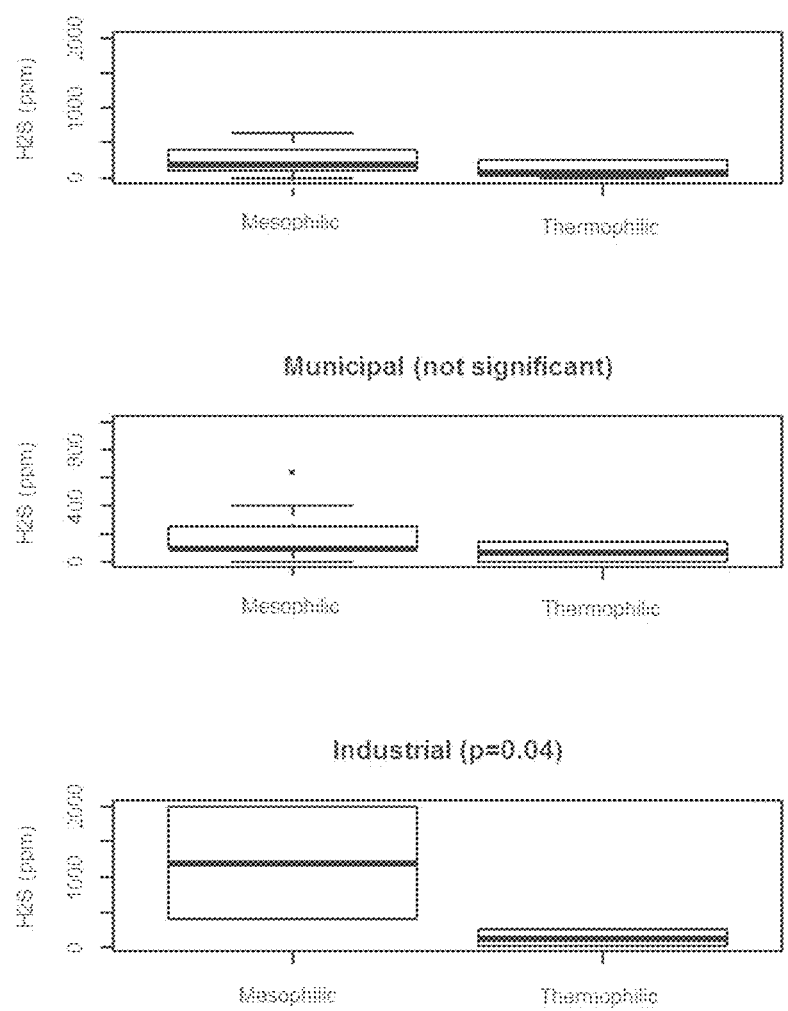
FIG. 24 is a second example of a boxplot depicting the effect of mesophilic/thermophilic for industry vs. municipal.

As shown in FIG. 24, industrial mesophilic digesters contains greater amounts of hydrogen sulfide than industrial thermophilic digesters. However, the difference in hydrogen sulfite amounts between municipal mesophilic digesters and municipal thermophilic digesters is far less marked.

Figure 25:
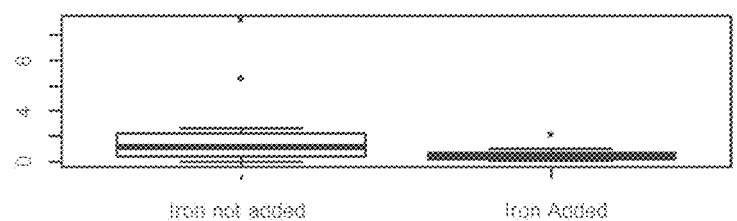
FIG. 25 is a first example of a boxplot depicting the effect of iron addition for industry vs. municipal.
Figure 25:
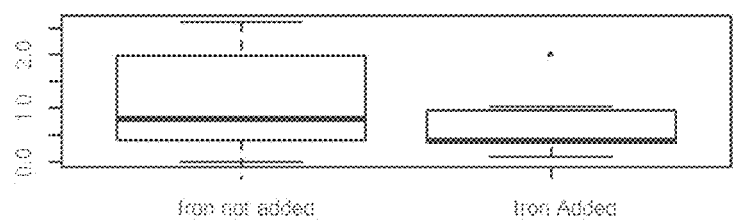
Figure 25:
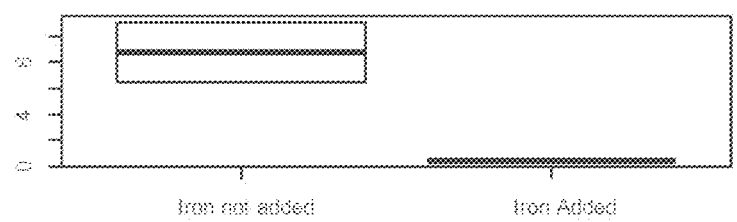
Figure 26:
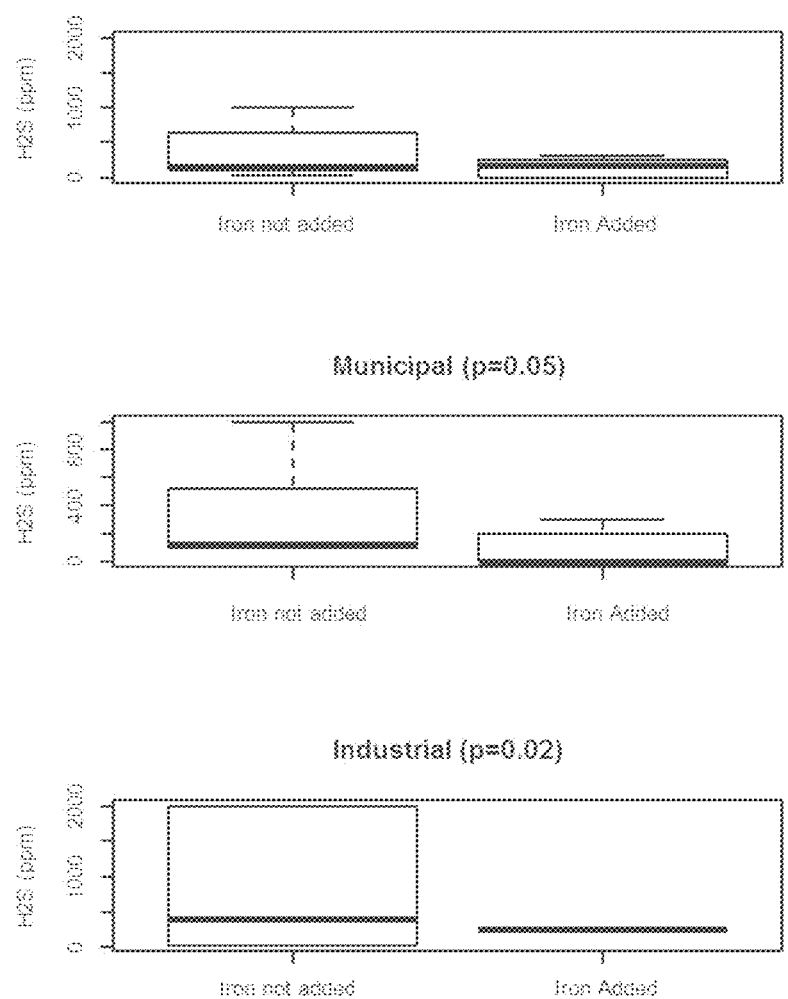
FIG. 26 is a second example of a boxplot depicting the effect of iron addition for industry vs. municipal.

As shown in FIG. 25, the addition of iron correlates with decreased biogas production in digesters. As shown in FIG. 26, the addition of iron correlates with decreased production of hydrogen sulfite. These differences are statistically significant when all digesters are analyzed together.

Figure 27:
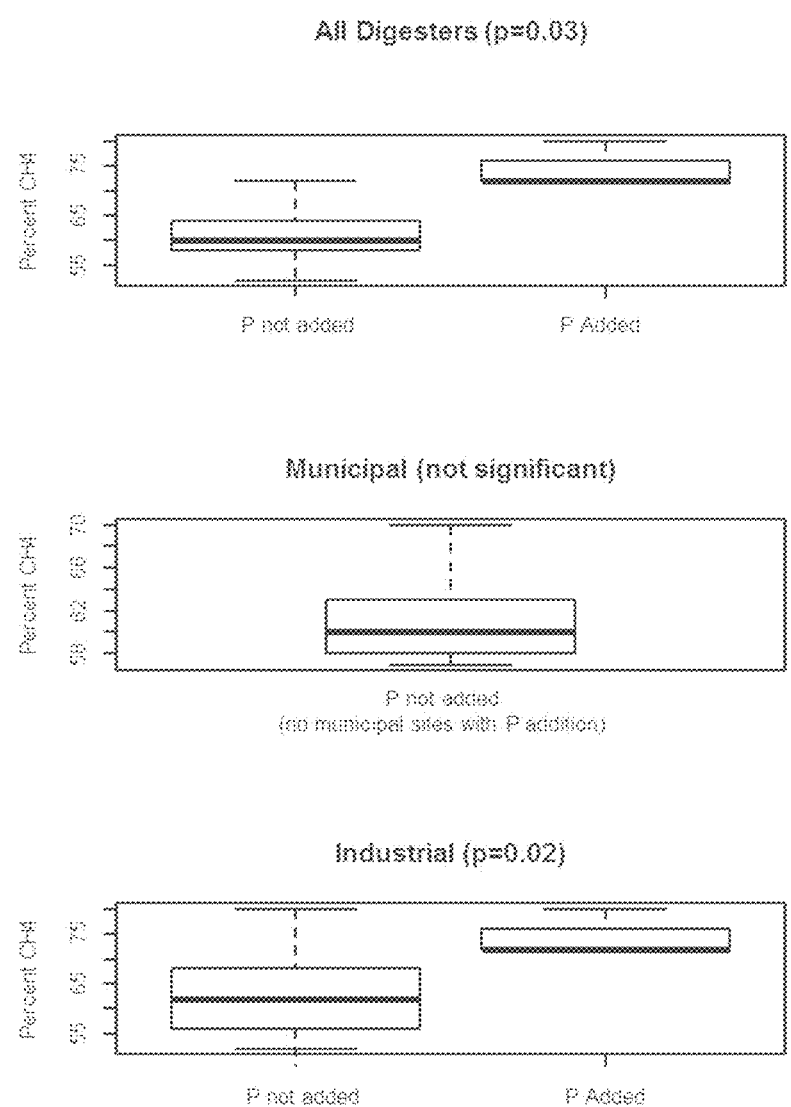
FIG. 27 is a first example of a boxplot depicting the effect of phosphorus addition for industry vs. municipal.
Figure 28:
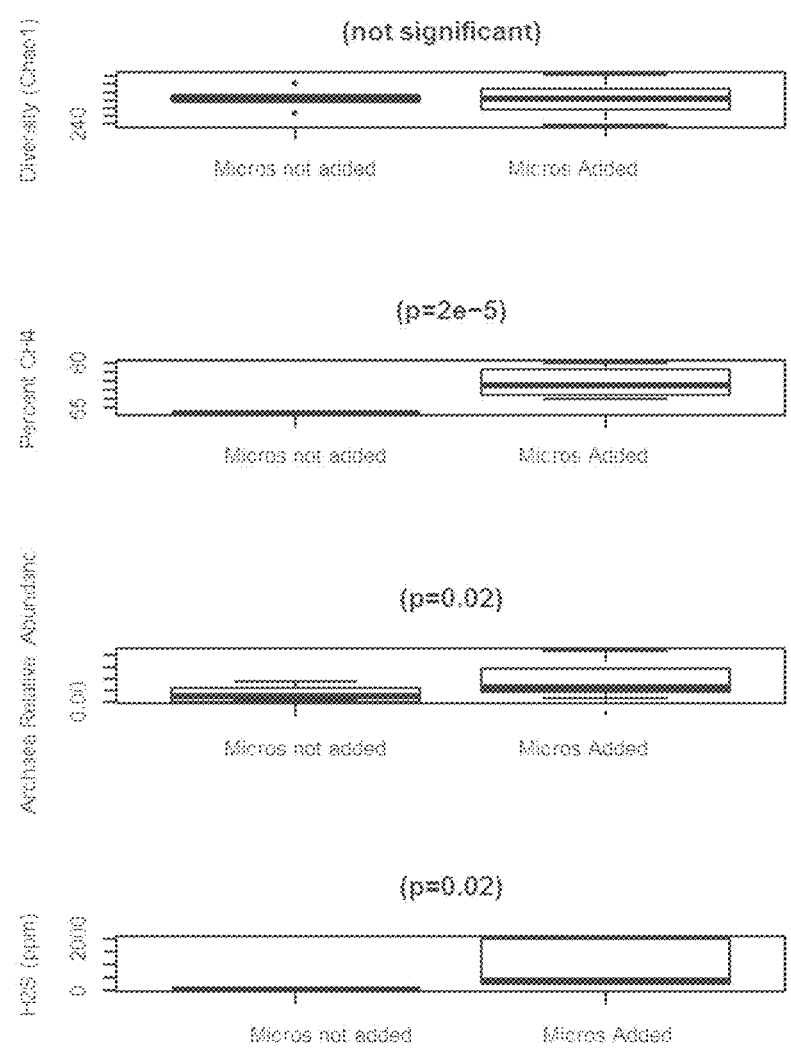
FIG. 28 is a second example of a boxplot depicting the effect of micronutrients (micros) added to industry vs. municipal reactors.

As shown in FIG. 27, the addition of phosphorus correlates with an increase in the percentage of methane in digesters. This difference is statistically significant in all digesters and in industrial digesters, but was not determined in municipal digesters. As shown in FIG. 28, the addition of micronutrients (micros) results in measurable increases in hydrogen sulfite, Archea relative abundance, and percent methane, but in no significant difference in microbial diversity.

Figure 29:
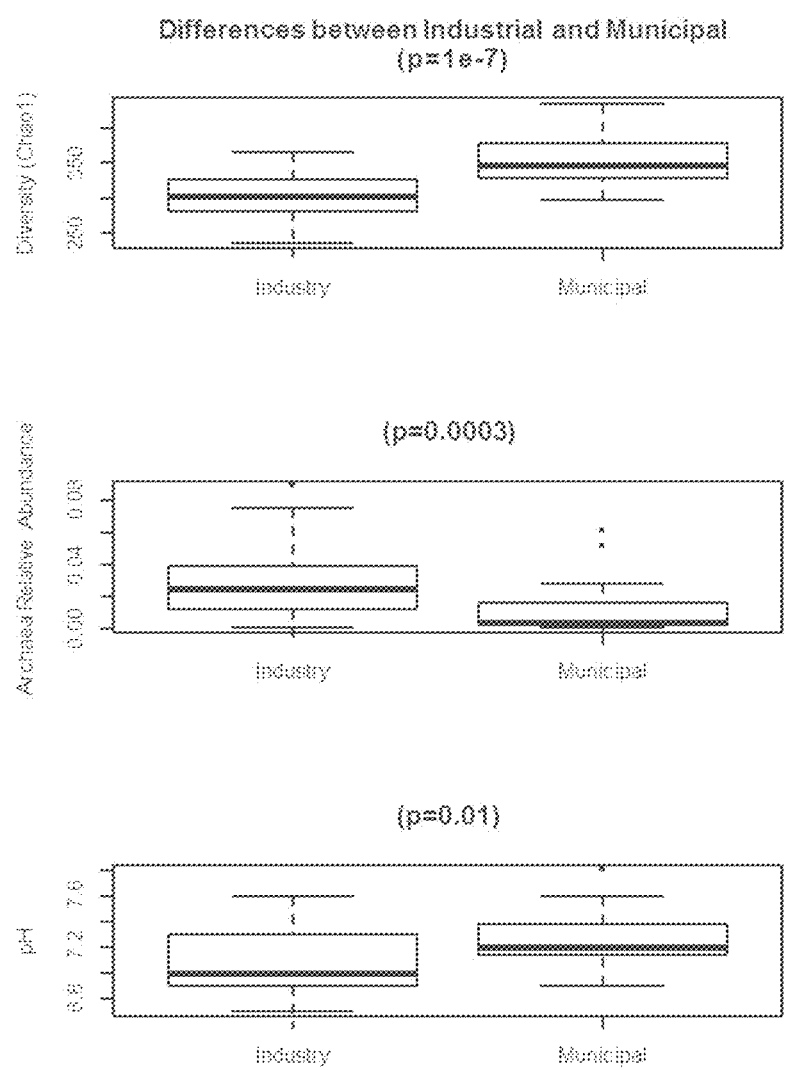
FIG. 29 is an example of a boxplot comparing diversity, archaea, and pH for industry vs. municipal.

As shown in FIG. 29, industrial and municipal digesters showed differences in diversity, Archea relative abundance, and pH.

Figure 30:
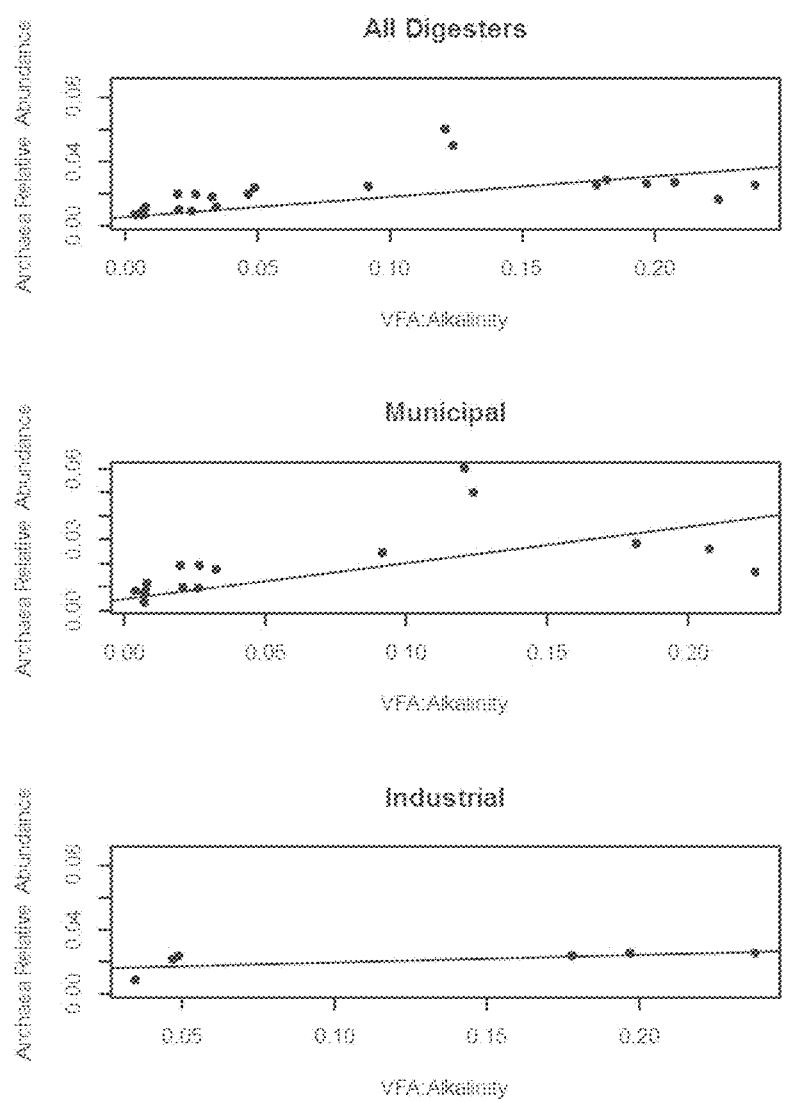
FIG. 30 is a first example of a graph of VFA:alkalinity and archea relative abundance for industry vs. municipal.
Figure 31:
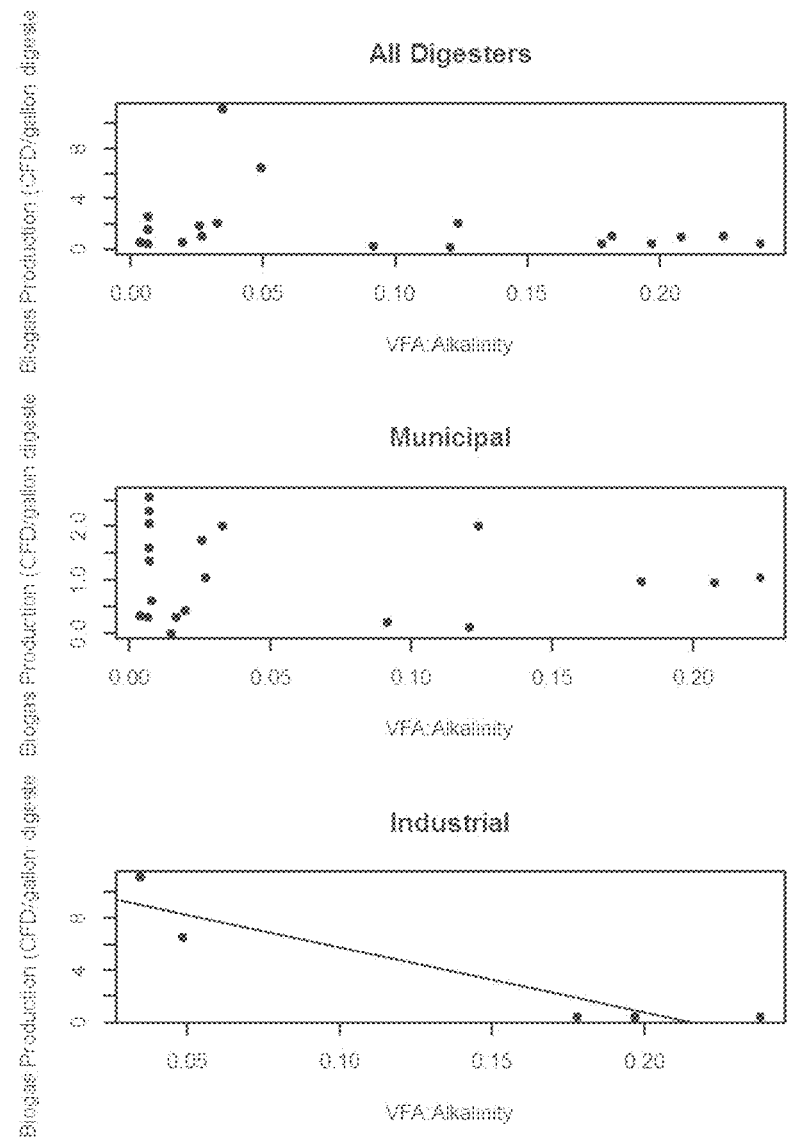
FIG. 31 is a second example of a graph of VFA:alkalinity for industry vs. municipal.
Figure 32:
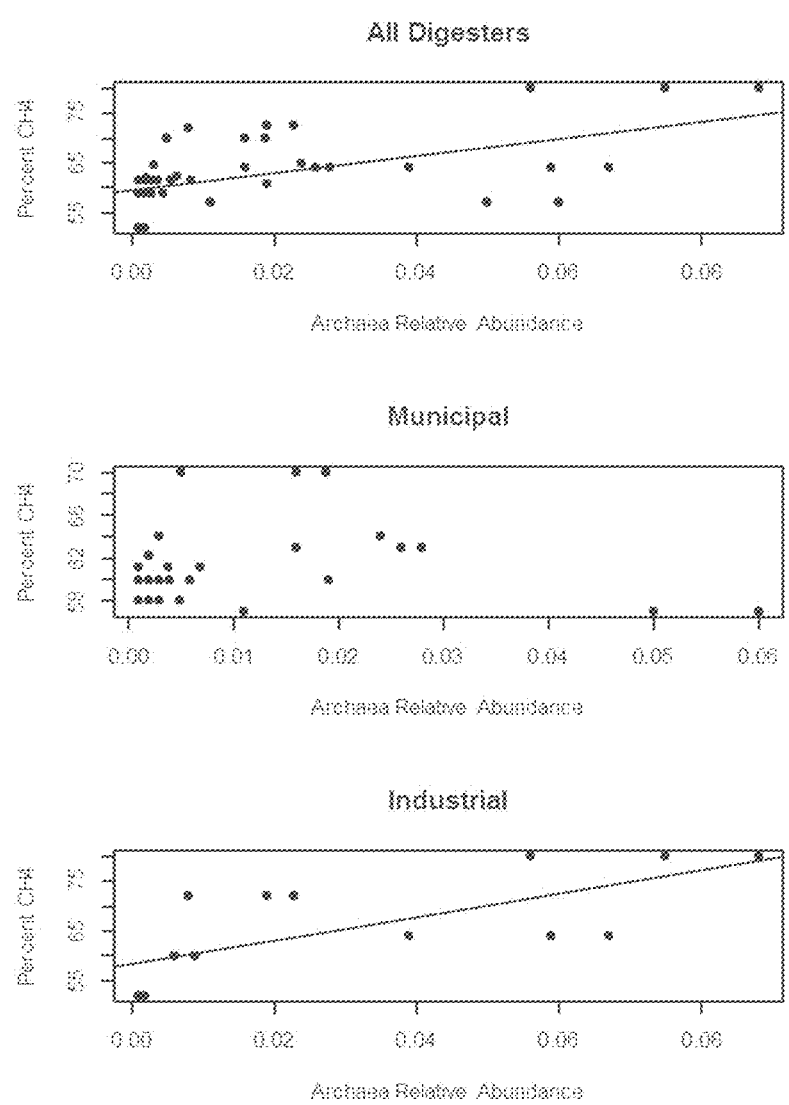
FIG. 32 is a first example of a graph of factors affecting methane production for industry vs. municipal.
Figure 33:
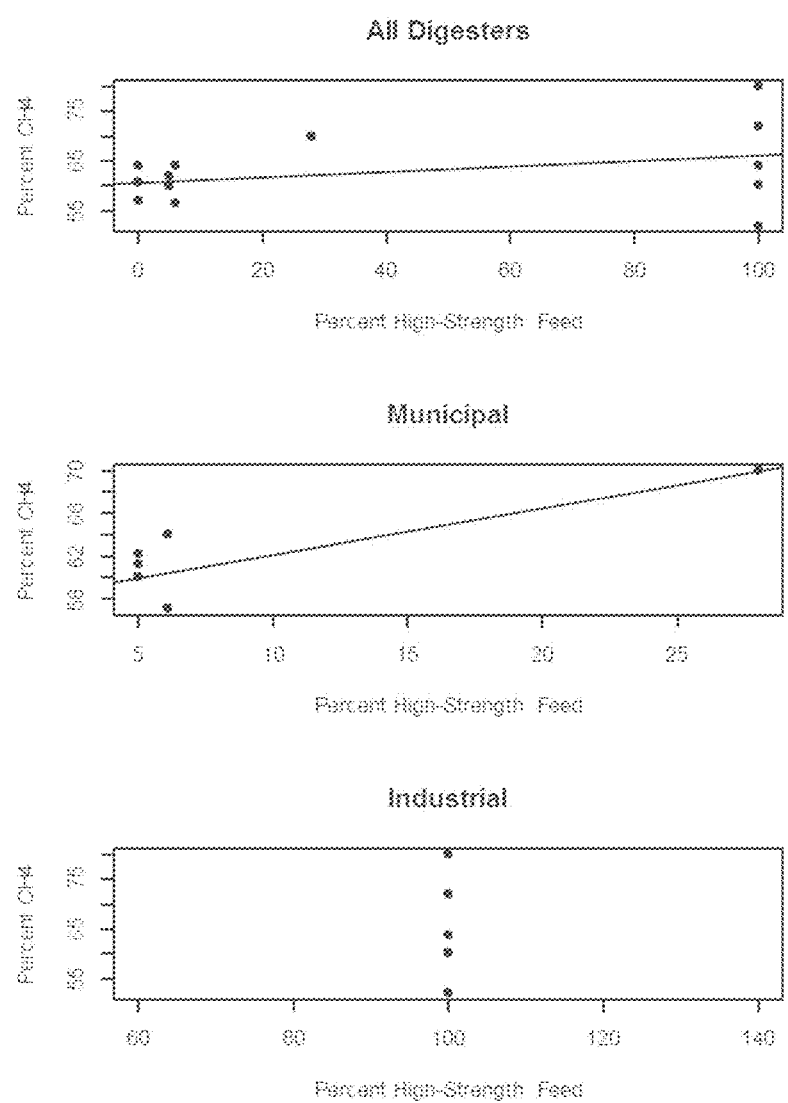
FIG. 33 is a second example of a graph of factors affecting methane production for industry vs. municipal.
Figure 34:
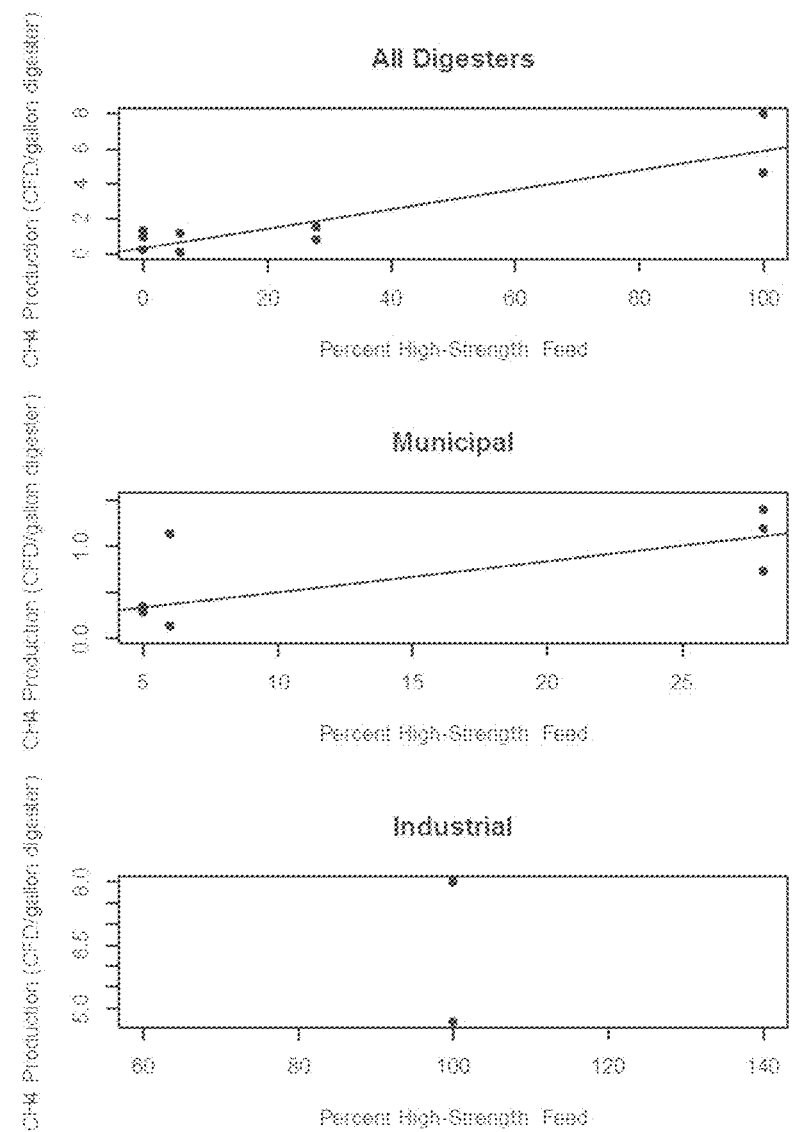
FIG. 34 is a third example of a graph of factors affecting methane production for industry vs. municipal.

As shown in FIG. 30, the Archea relative abundance and VFA:alkalinity correlated differently to each other in municipal digesters compared to industrial digesters.

Figure 35:
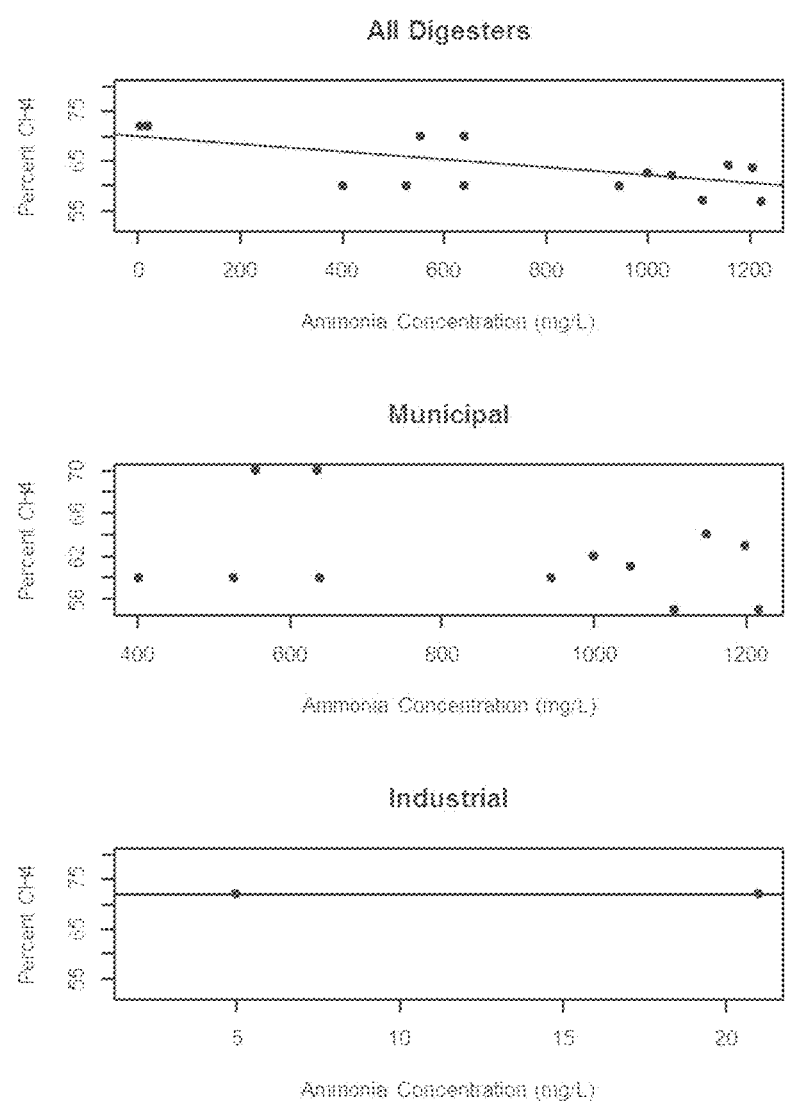
FIG. 35 is a fourth example of a graph of factors affecting methane production for industry vs. municipal.
Figure 36:
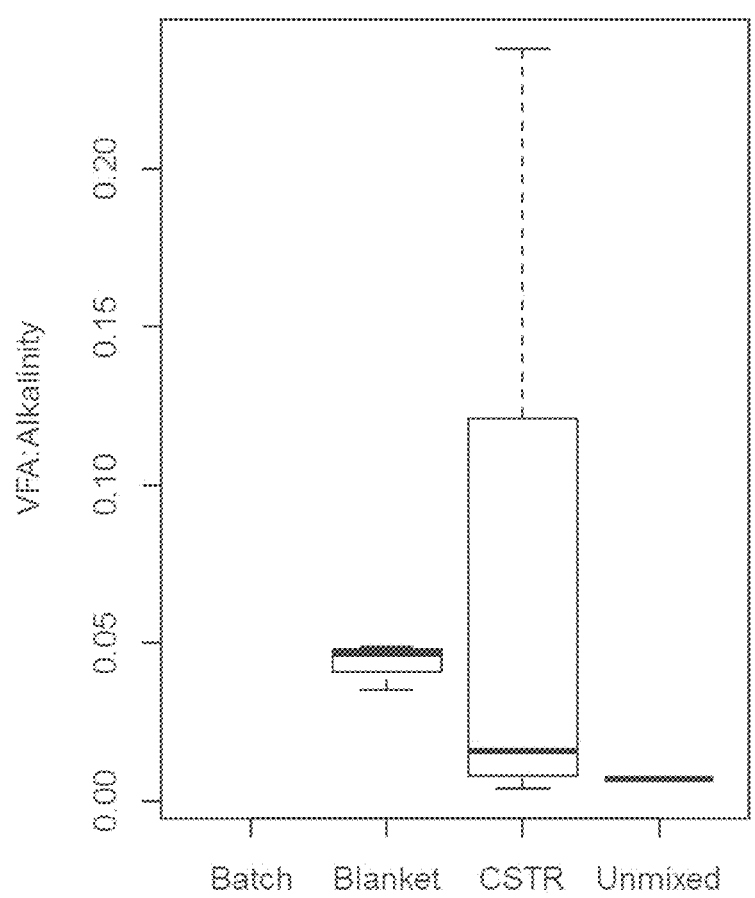
FIG. 36 is a first example of a boxplot depicting the effect of different mixing regimes on VFA:alkalinity.
Figure 37:
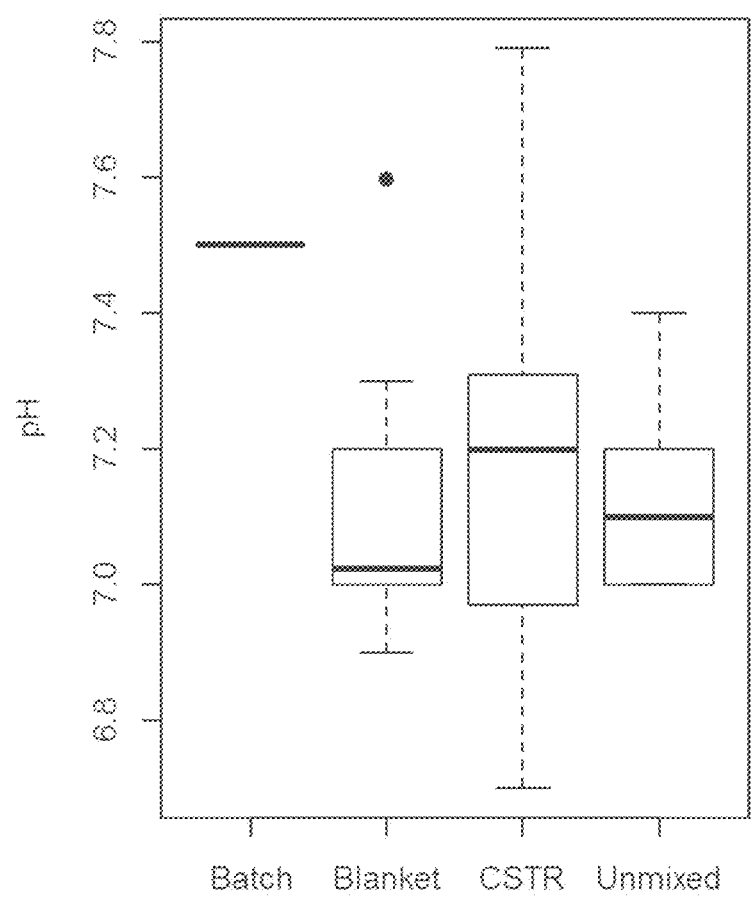
FIG. 37 is a second example of a boxplot depicting the effect of different mixing regimes on pH.
Figure 38:
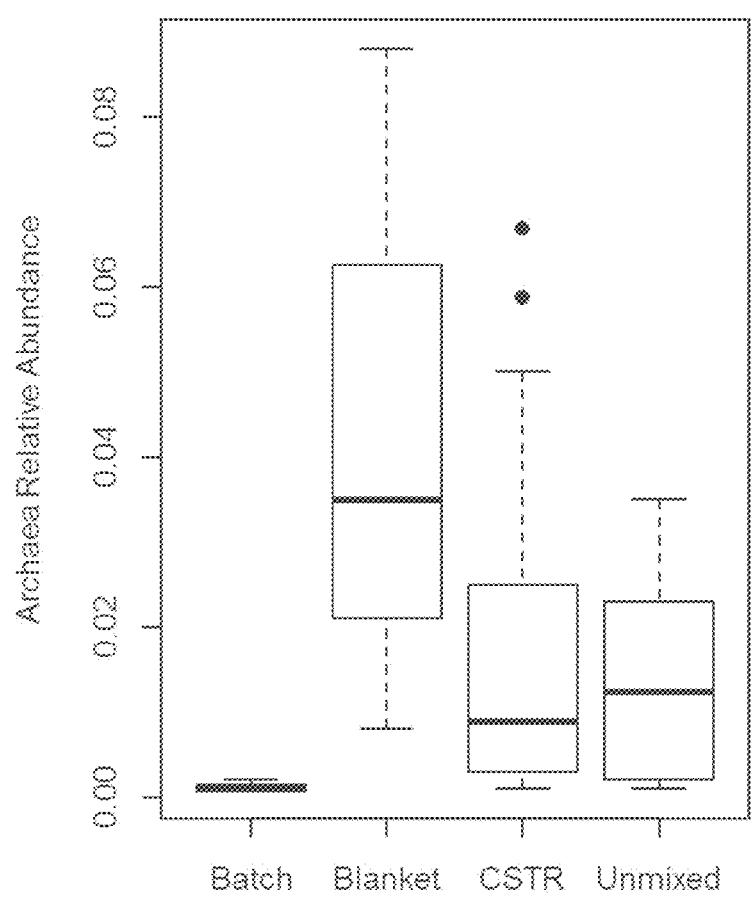
FIG. 38 is a third example of a boxplot depicting the effect of different mixing regimes on archea relative abundance.
Figure 39:
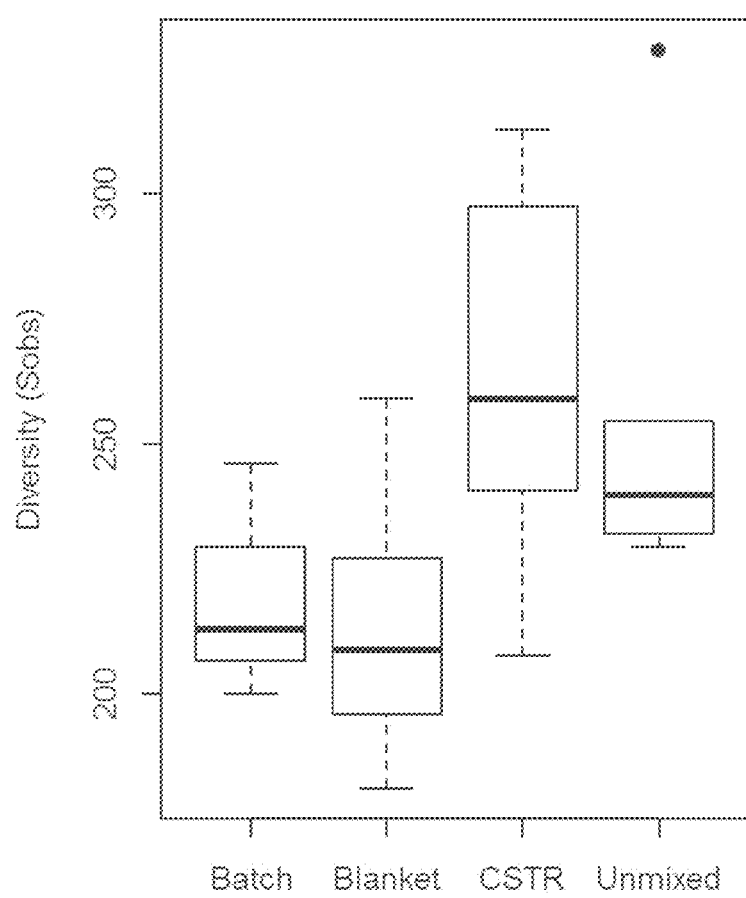
FIG. 39 is a fourth example of a boxplot depicting the effect of different mixing regimes on diversity.
Figure 40:
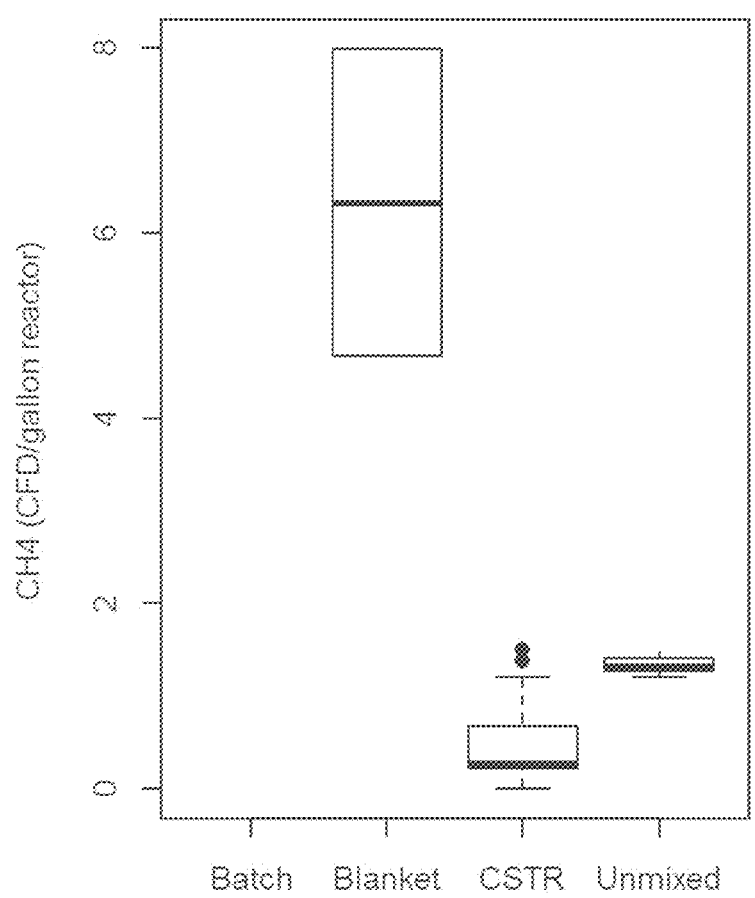
FIG. 40 is a fifth example of a boxplot depicting the effect of different mixing regimes on methane production.
Figure 41:
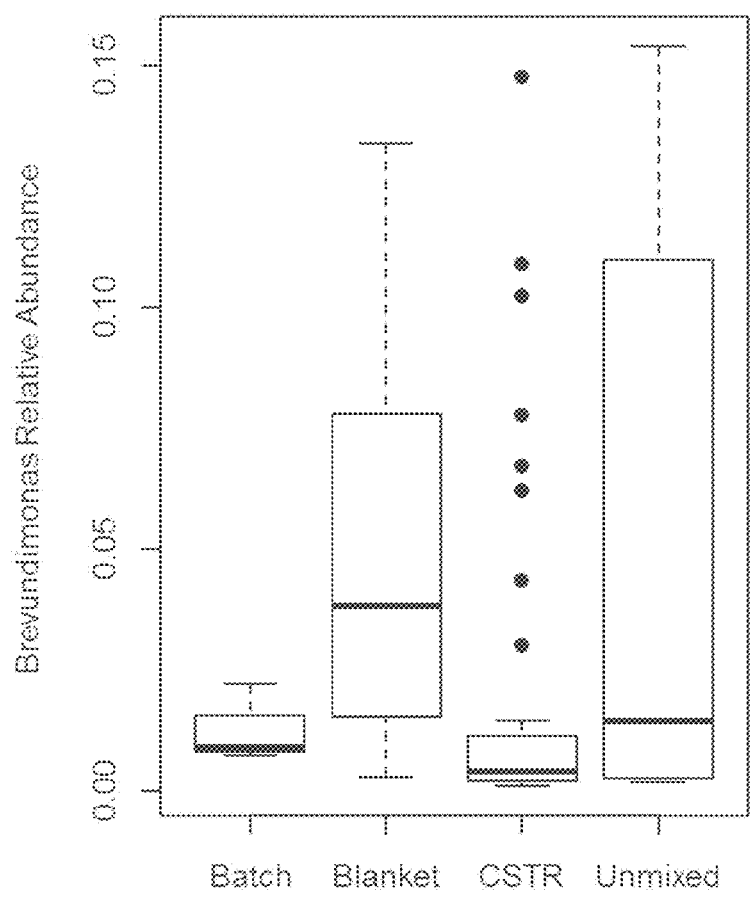
FIG. 41 is a sixth example of a boxplot depicting the effect of different mixing regimes on the relative abundance of *Brevundimonas*.
Figure 42:
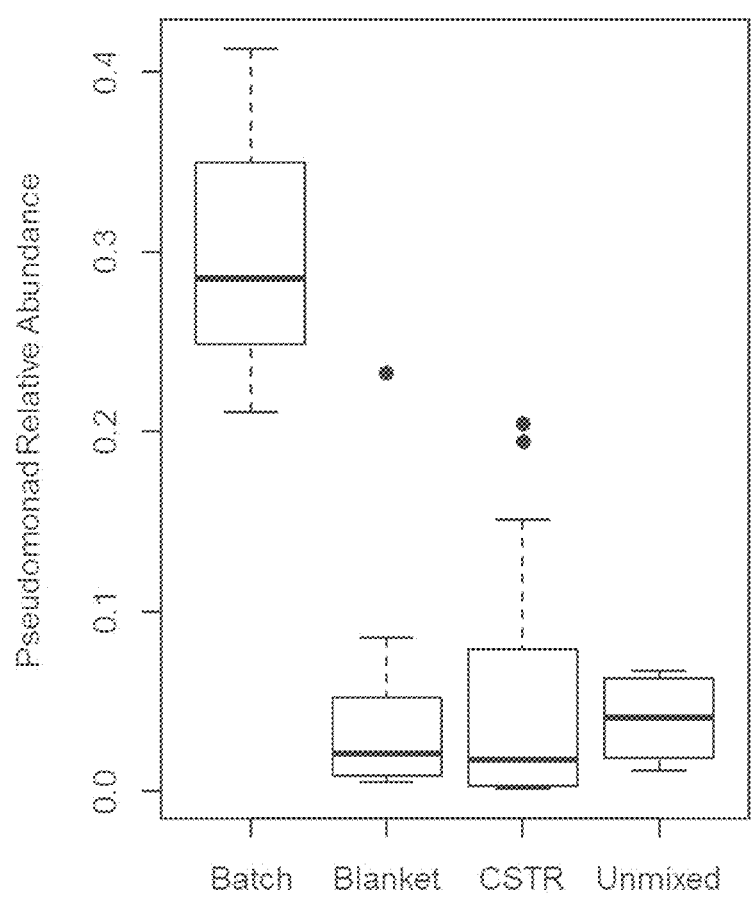
FIG. 42 is a seventh example of a boxplot depicting the effect of different mixing regimes on the relative abundance of *Pseudomonad*.
Figure 43:
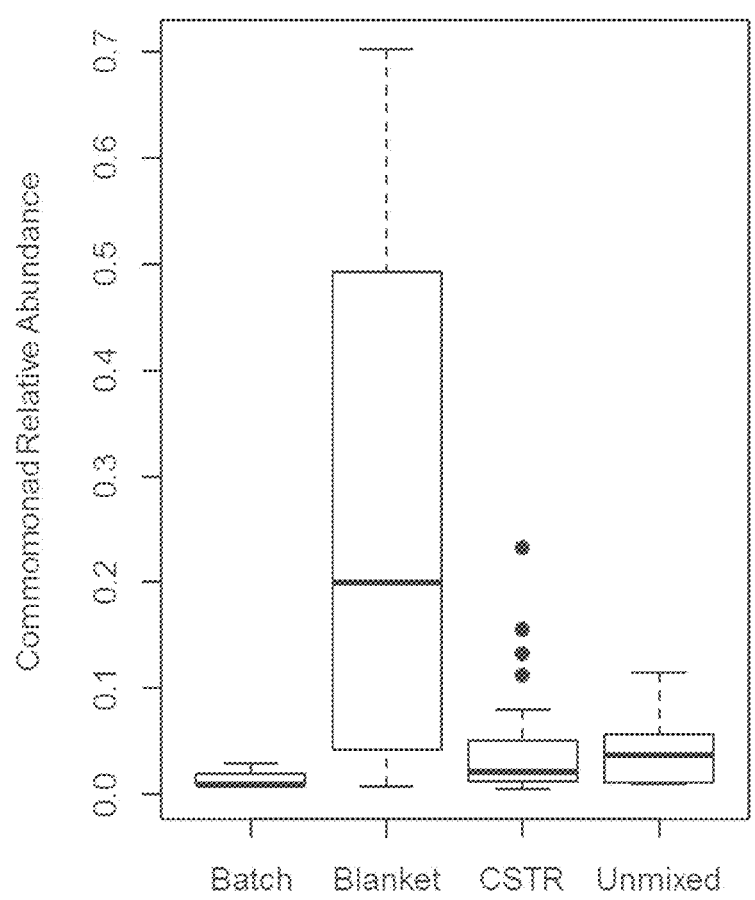
FIG. 43 is an eighth example of a boxplot depicting the effect of different mixing regimes on the relative abundance of *Commomonad*.
Figure 44:
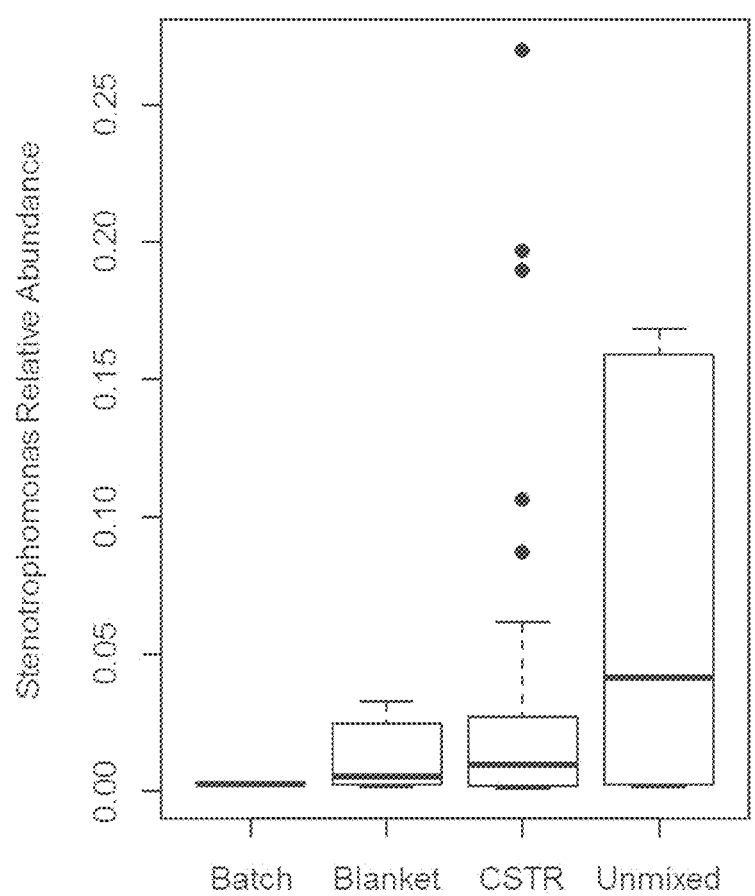
FIG. 44 is a ninth example of a boxplot depicting the effect of different mixing regimes on the relative abundance of *Stenotrophomonas*.

FIGS. 31-35 provide insight about the correlation between different chemical and microbiological parameters to the production (and recovery of) biogases in microbial waste systems. The correlation of biogas or methane production is compared to VFA:alkalinity (FIG. 31), Archea relative abundance (FIG. 32), percentages of high-strength feed (FIGS. 33-34), and ammonia concentration (FIG. 35). In each, digesters are considered as a group, or divided into municipal digesters or industrial digesters. As shown elsewhere, the municipal digesters exhibited different results compared to industrial digesters.

Figure 45:
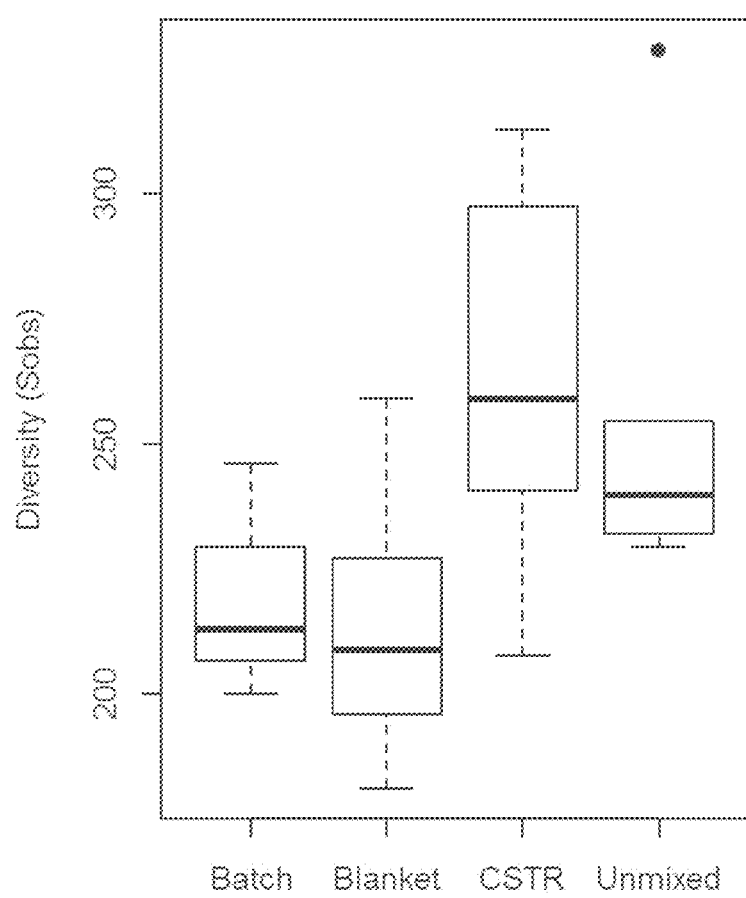
FIG. 45 is a tenth example of a boxplot depicting the effect of different mixing regimes on microbial diversity.

Reactors operate using different types of anaerobic reactors, including catch reactors, blanket reactors, continuously stirred tank reactors ("CSTR"), and unmixed reactors. As shown in FIGS. 36-45, these different reactors exhibit different profiles for their chemical and microbiological characteristics, such as VFA:alkalinity (FIG. 36), pH (FIG. 37), Archea relative abundance (FIG. 38), microbial diversity (FIG. 39), methane content (FIG. 40), *Brevundimonas* relative abundance (FIG. 41), *Pseudomonad* relative abundance (FIG. 42), *Commomonad* relative abundance (FIG. 43), *Stenotrophomonas* relative abundance (FIG. 44), and diversity (FIG. 45). Each type of anaerobic reactor generates a unique profile for these characteristics.

Figure 46:
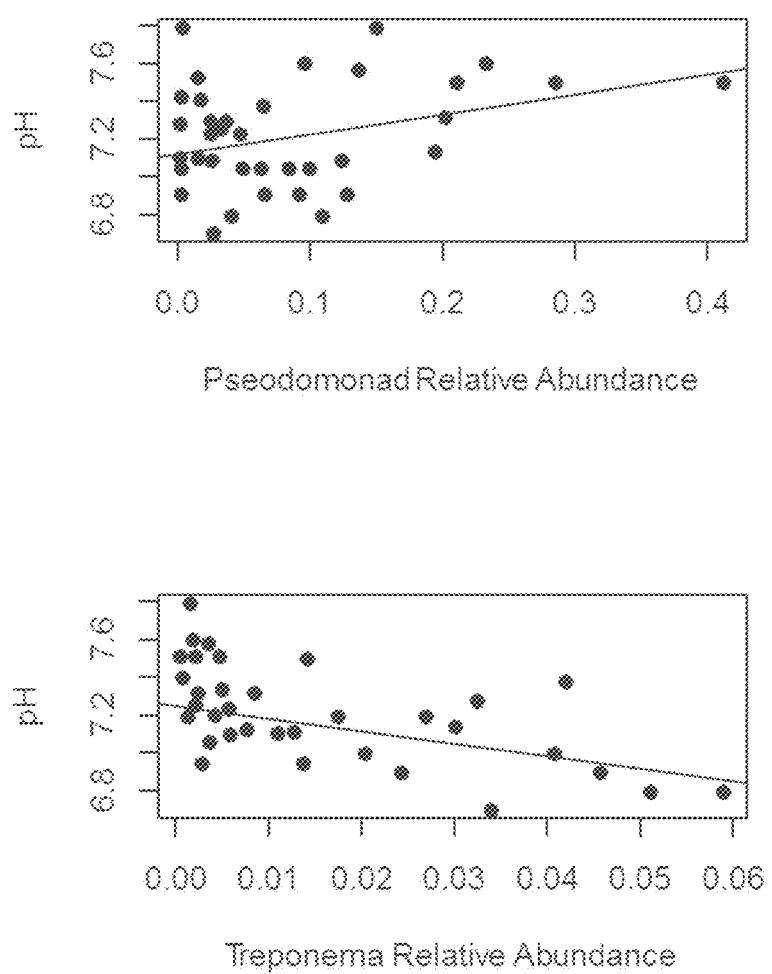
FIG. 46 is a first example of graphs depicting the correlation between pH and the relative abundance of different microbial groups.
Figure 47:
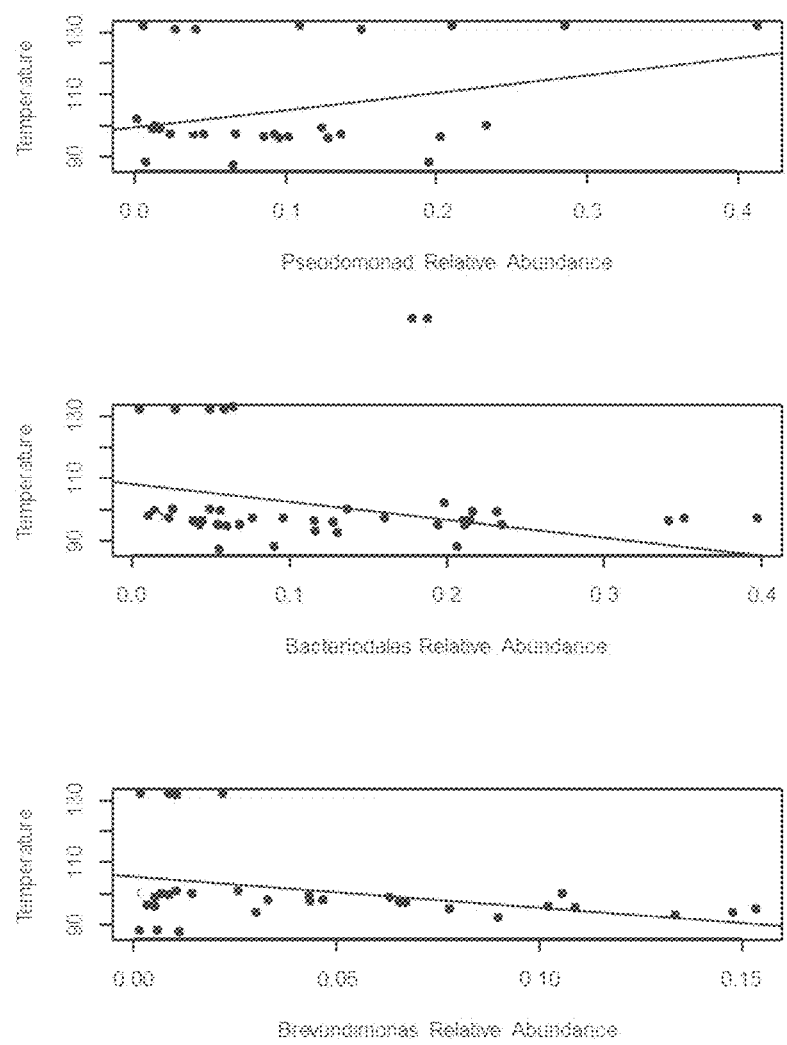
FIG. 47 is a second example of graphs depicting the correlation between temperature and the relative abundance of different microbial groups.
Figure 48:
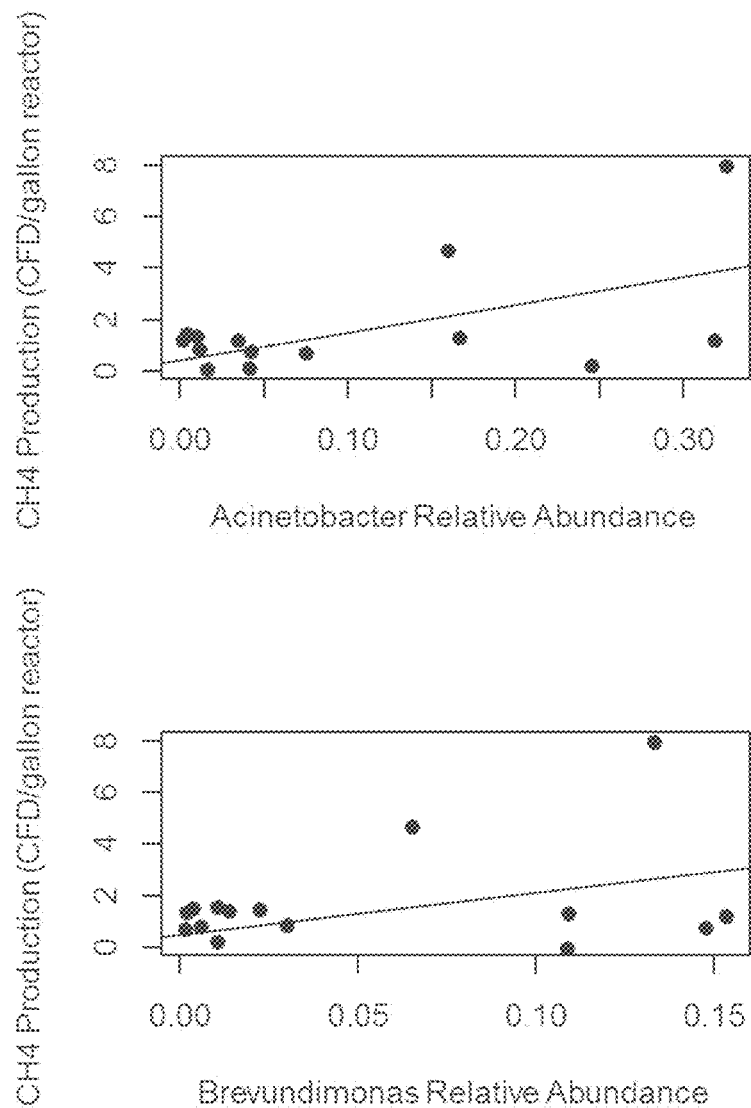
FIG. 48 is a third example of graphs depicting the correlation between microbial groups and methane production.

As shown in FIGS. 46-47, temperature and pH affects the abundance of different bacterial groups in different ways and different degrees. As shown in FIG. 48, the abundance of certain microbial groups is positively correlated with methane production.

Figure 49:
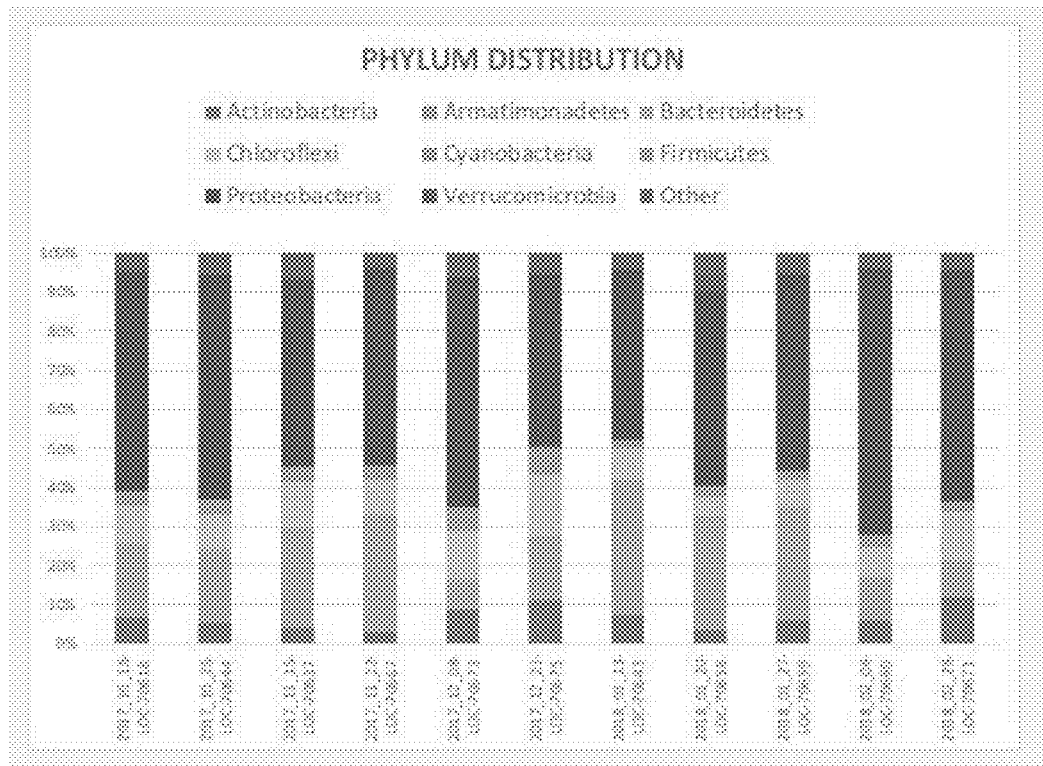
FIG. 49 is a chart showing phylum distribution results communicated in a microbiome digital signature report concerning biological nutrient removal accordance with one embodiment of the invention.
Figure 50:
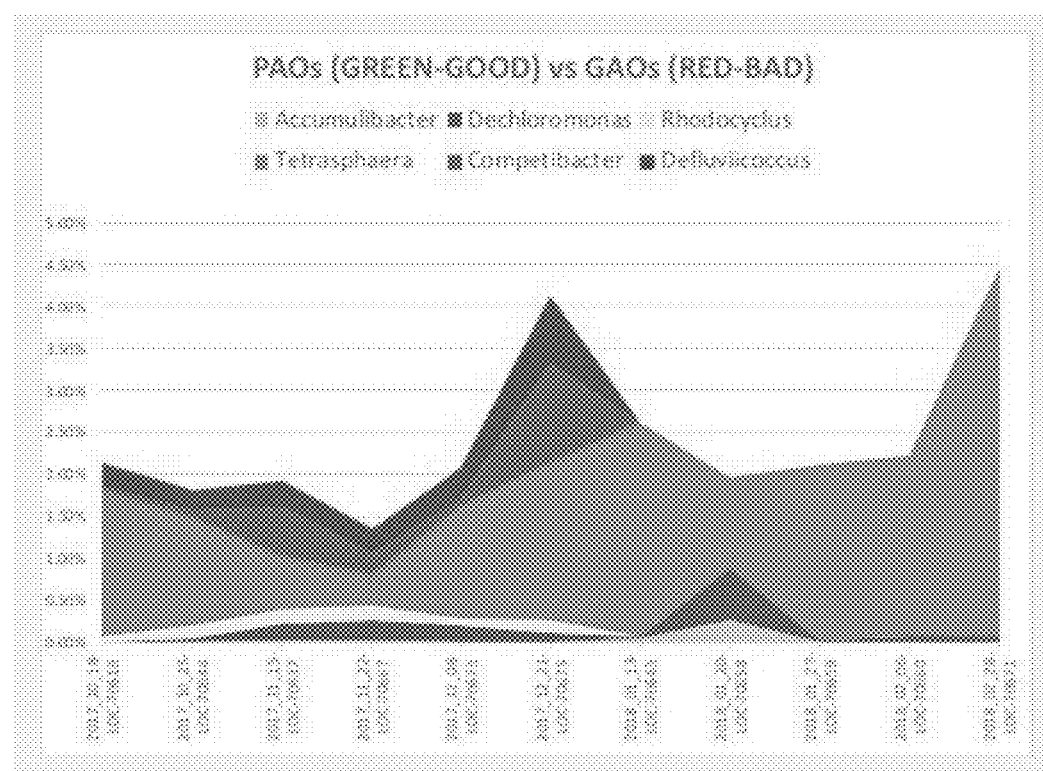
FIG. 50 is a chart showing phosphorus-reducing microbe results communicated in a microbiome digital signature report concerning biological nutrient removal in accordance with one embodiment of the invention.

In one embodiment in accordance with the present invention, information can be can be communicated in DNA analysis and microbiome digital signature report. In one embodiment such analysis is specialized for measuring and monitoring the ecology of Biological Nutrient Removal (BNR) systems in a wastewater treatment facility for the purpose of optimizing the facility's performance. In one embodiment, all nitrogen and phosphorous consuming microbes previously present in a sample and listed in known databases can identified, along with a quantification of percent prevalence. In one embodiment, Phosphorus Accumulating Organisms (PAO) and Glycogen Accumulating Organisms (GAO) can be tracked on a dashboard (similar to the one shown in FIG. 10) including a trend analysis over time. In one embodiment, ammonia-oxidizing bacteria (AOB) and nitrite-oxidizing bacteria (NOB) are tracked for nitrogen removal programs. In one embodiment, the top ten microbes based on percent prevalence are identified plus many others important in wastewater treatment, and a complete listing of all microbes identified. Referring now to FIG. 49, a chart is depicted showing phylum distribution results communicated in a microbiome digital signature report concerning biological nutrient removal accordance with one embodiment of the invention. Referring now to FIG. 50, a chart is depicted showing PAOs vs GAOs results communicated in a microbiome digital signature report concerning biological nutrient removal in accordance with one embodiment of the invention.

It should be understood, of course, that the foregoing relates to exemplary embodiments of the invention and that modifications can be made without departing from the spirit and scope of the invention as set forth in the following claims Embodiments of the present invention are not limited to the particular details of the method/embodiment depicted, and other modifications and applications are contemplated. Certain other changes can be made in the above-described method without departing from the true spirit and scope of the invention herein involved. For example, the present method can be utilized with other types of liquid transport or storage systems, such as water fountains, closed buildings, pools, irrigation systems, waste treatment systems. It is intended, therefore, that the subject matter in the above depiction shall be interpreted as illustrative and not in a limiting sense.

The invention claimed is:

1. A method of recovering resources from a microbe supporting waste stream comprising:
   receiving a sample taken from a microbe supporting waste stream,
   obtaining a microbial DNA analysis of the sample using microbial DNA sequencing,
   the microbial DNA analysis including a listing of microbial DNA found in the sample,
   the listing of microbial DNA including parts of microbial DNA uniquely identifying microbes,
   identifying a microbial content of the microbe supporting waste stream by comparing the listing of microbial DNA found in the sample to a list of known microbial DNA to identify microbes present in the sample and assessing a prevalence of the microbes present in the sample,
   comparing the microbial content to an optimal balance of microbes associated with a specific effort to recover a resource to identify adjustments to microbial content of the microbe supporting waste stream based on the identification of the microbes in the sample, wherein said adjustments to the microbial content will recover the resource from the microbe supporting waste stream, and
   wherein the optimal balance documents an optimal presence and optimal prevalence of the microbes associated with the specific effort to recover the resource.

2. The method of claim 1 wherein the microbe supporting waste stream is a water system.

3. The method of claim 2 wherein the water system is a wastewater treatment system.

4. The method of claim 1 wherein said adjustment comprises adding a compound to the microbial supporting environment, the compound for cultivating one or more identified microbes.

5. The method of claim 4 wherein the compound is phenol.

6. The method of claim 3 wherein obtaining a microbial DNA analysis further comprises extracting a microbial DNA sequence, the microbial DNA sequence having a hypervariable region unique to a microbe; amplifying a portion of the hypervariable region of the microbial DNA sequence;
   and determining the sequence of the amplified portion.

7. The method of claim 6 wherein the resource recovered comprises clean water.

8. The method of claim 6 wherein the resource recovered comprises biogas.

9. The method of claim 8 wherein the biogas is methane.

10. The method of claim 6 wherein the resource recovered comprises water contaminants.

11. The method of claim 10 wherein the adjustments to the microbial content of the microbe supporting environment includes identifying microbes for processing the water contaminants.

12. The method of claim 11 wherein the water contaminant is nitrogen.

13. The method of claim 11 wherein the water contaminant is phosphorus.

14. A method of recovering resources from a wastewater treatment system, the method comprising:
   receiving a sample taken from a wastewater treatment system,
   obtaining a microbial DNA analysis of the sample using microbial DNA sequencing,
   the microbial DNA analysis including a listing of microbial DNA found in the sample,
   the listing of microbial DNA including parts of microbial DNA uniquely identifying microbes,
   identifying a microbial content of the wastewater treatment system by comparing the listing of microbial DNA found in the sample to a list of known microbial DNA to identify microbes present in the sample and assessing a prevalence of the microbes present in the sample, and
   comparing the microbial content to an optimal balance of microbes associated with a specific effort to recover a resource to identify adjustments to the microbial content of the wastewater treatment system based on the identification of the microbes in the sample, wherein said adjustments to the microbial content of the wastewater treatment system will recover the resource from the wastewater treatment system, and wherein the optimal balance documents an optimal presence and optimal prevalence of the microbes associated with the specific effort to recover the resource.

15. The method of claim 14, wherein the resource recovered is selected from the group consisting of clean water, methane, and water contaminants, and combinations thereof.

16. The method of claim 14 wherein the sample is a liquid sample.

17. The method of claim 14 wherein the sample is a solid sample.

18. The method of claim 16 wherein the liquid sample is passed through a filter to concentrate microbes in the sample.

19. A method comprising:
receiving a sample taken from a microbe supporting source,
obtaining a microbial DNA analysis of the sample using microbial DNA sequencing,
the microbial DNA analysis including a listing of microbial DNA found in the sample,
the listing of microbial DNA including parts of microbial DNA uniquely identifying microbes,
identifying a microbial content of the microbe supporting source by comparing the listing of microbial DNA found in the sample to a list of known microbial DNA to identify microbes present in the sample,
comparing the microbial content to an optimal balance of microbes associated with a specific effort to recover a resource to identify adjustments to microbial content of the source based on the identification of the microbes in the sample, wherein said adjustments to the microbial content will recover the resource from the source, and
wherein the optimal balance documents an optimal presence of the microbes associated with the specific effort to recover the resource.

20. The method of claim 19, wherein the resource recovered is selected from one of clean water, methane, water contaminants, or combination thereof.

* * * * *